United States Patent [19]
Lin

[11] Patent Number: 5,491,236
[45] Date of Patent: Feb. 13, 1996

[54] (1,2N) AND (3,2N)-CARBOCYCLIC-2-AMINO TETRALIN DERIVATIVES

[75] Inventor: Chiu-Hong Lin, Kalamazoo, Mich.

[73] Assignee: The Upjohn Company, Kalamazoo, Mich.

[21] Appl. No.: 803,287

[22] Filed: Dec. 4, 1991

Related U.S. Application Data

[63] This application is a continuation of PCT/US90/03551, Jun. 27, 1990, which is a continuation of Ser. No. 379,526, Jul. 13, 1989, abandoned.

[51] Int. Cl.$^6$ .................... C07D 209/60; A61K 31/40
[52] U.S. Cl. ................... 546/101; 546/99; 548/427; 548/450
[58] Field of Search .................... 548/420, 427, 548/450; 546/99, 101

[56] References Cited

U.S. PATENT DOCUMENTS

| | | | |
|---|---|---|---|
| 4,234,731 | 11/1980 | Kavadias | 548/427 |
| 4,618,683 | 10/1986 | De Bernadis et al. | 548/420 |
| 5,030,636 | 7/1991 | Imhof et al. | 546/101 |
| 5,180,733 | 1/1993 | Basha et al. | 514/410 |
| 5,244,888 | 9/1993 | De Bernards et al. | 548/427 |
| 5,248,677 | 9/1993 | Basha et al. | 514/217 |
| 5,318,966 | 6/1994 | Brudener et al. | 514/232.8 |
| 5,318,967 | 6/1994 | Brudener et al. | 514/232.8 |

FOREIGN PATENT DOCUMENTS

| | | |
|---|---|---|
| 0059553 | 9/1982 | European Pat. Off. . |
| 0127597 | 12/1984 | European Pat. Off. . |
| 272534 | 8/1988 | European Pat. Off. . |
| 548664 | 6/1993 | European Pat. Off. . |
| 2146503 | 3/1973 | France . |
| 1555553 | 8/1984 | France . |
| 2044172 | 3/1971 | Germany . |
| 2134515 | 8/1984 | United Kingdom . |

OTHER PUBLICATIONS

A. Kumar, et al., "Studies on analgesic–narcotic antagonists: synthesis of N–substituted 1,2,3,4,4a,5,6, 10b–octahydrobenzo[f]–quinolines", p. 456, abstract 5285g, Chemical Abstracts, vol. 86, 1977 & Indian J. Chem, Sect. B 1976 14B(7), 556–7.

H. Wikstrom et al., "N–substituted 1,2,3,4,4a,5,6, 10b–octhydrobenzo[f]quinolines and 3–phenylpiperindes: effects on central dopamine and βreceptors", pp. 2169–2174 (see compounds 11–33) Journal of Medicnal Chemistry, vol. 30, No. 12, 1987, American Chemical Society.

J. G. Cannon et al., "Rigid congeners of dopamine based on octahydrobenzo[f]quinoline: peripheral and central effects" pp. 341–347 (see compounds 1–7, 13–16) Journal of Medicinal Chemistry, vol. 22, No. 4, 1979, American Chemical Society.

J. G. Cannon et al., "Congeners of the βconformer of dopamine derived from cis– and trans–octahydrobenzo[f] quinoline and trans–octahydrobenzo[f]quinoline and trans–octahydrobenzo[g]quinoline", pp. 1–5 (see Table I), Journal of Medicinal Chemistry, vol. 213, No. 1, Jan. 1980, American Chemical Society.

H. Wikstrom et al., "Monophenolic octahydrobenzo[f] quinolines: central dopamine— and serotonin–receptor stimulating activity" pp. 925–931 (see compounds 6–19) Journal of Medicinal Chemistry, vol. 25, No. 8, 1982 American Chemical Society.

J. G. Cannon et al., "Conformationally restriced congeners of dopamine derived from octahydrobenzo[g]quinoline and octahydrobenzo[f]quinoline " pp. 190–195 (see compounds 16, 42–50) Journal of Medicinal Chemistry, vol. 27, No. 2, 1984, American Chemical Society.

J. G. Cannon et al., "p–dimethoxy–substituted trans–octahydrobenzo[f]and —[g ]quinolines: synthesis and assessment of dopaminergic agonist effects" pp. 2529–2534 (see compounds 8,9,13)Journal of Medicinal Chemistry, vol. 29, No. 12, 1986, American Chemical Society.

J. G. Cannon et al., "Assessment of a potential dopaminergic prodrug moiety in several ring systems", pp. 2016–2020(see compounds 4a–4d) Journal of Medicinal Chemistry, vol. 29, No. 10, 1986, American Chemical Society.

H. Wikstrom et al., "Resolved cis–10–hydroxy–4–n–propyl–1,2,3,4,4a,5,6, 10b–octahydrobenzo f quinoline: central serotonin stimulating properties"pp. 1567–1573 (see p. 1567) Journal of Medicinal Chemistry, vol. 30, No. 9, Sep. 1987, American Chemical Society.

Primary Examiner—Nicholas Rizzo
Attorney, Agent, or Firm—Donald L. Corneglio

[57] ABSTRACT

This invention is therapeutically useful tetralins and pharmaceutically acceptable acid addition salts thereof of the formula

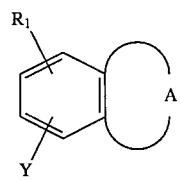

wherein R, $R_1$ and A are as defined in claim 1.

These compounds are useful to treat central nervous system disorders.

10 Claims, No Drawings

(1,2N) AND (3,2N)-CARBOCYCLIC-2-AMINO TETRALIN DERIVATIVES

CROSS REFERENCE TO RELATED APPLICATIONS

The present application is a continuation application of Ser. No. PCT/US90/03551, filed 27 Jun. 1990, now pending, which is a continuation-in-part of Ser. No. 07/379,526, filed 13 Jul. 1989, abandoned.

FIELD OF THE INVENTION

The present invention is related to new (1,2N) and (3,2N)-carbocyclic-2-amino- 1,2,3,4-tetrahydro-2-naphthylamines, to processes for preparing such compounds, pharmaceutical preparation of such compounds and the use of such compounds in manufacture of a pharmaceutical preparation.

BACKGROUND OF THE INVENTION

Psychiatric diseases are thought to be due to dysfunctions in monoaminergic neuronal systems, particularly those involving serotonin (5-HT) and dopamine (DA).

Anxiety is associated with increased activity in 5-HT systems. In animals where 5-HT has been depleted, benzodiazepine anxiolytics are not active in anti-anxiety assays that they otherwise are effective in. Seronotin neurons have autoreceptors that, when activated by agonists, depress firing rates of 5-HT cells. These receptors are of the $5\text{-HT}_{1A}$ subtype. Because they depress 5-HT neuronal activity, it can be expected that $5\text{-HT}_{1A}$ agonists will be an effective anxiolytic. Clinically, $5\text{-HT}_{1A}$ agonists have demonstrated anxiolytic properties. The drug Buspirone, is the only currently available marketed $5\text{-HT}_{1A}$ agonist having anxiolytic activity. This compound antagonizes dopamine receptors at the same dose it stimulates $5\text{-HT}_{1A}$ receptors. A similar drug, Gepirone, also has dopamine antagonist properties. These dopamine antagonist properties reduce the clinical utility of these compounds because long term treatment with dopamine antagonists can produce tardive dyskinesia.

Depression is a psychiatric condition thought to be associated with decreased 5-HT release. Most anti-depressants potentiate the effects of 5-HT by blocking the termination of activity through re-uptake into nerve terminals. Since some $5\text{-HT}_{1A}$ receptors are activated postsynaptically by 5-HT, $5\text{-HT}_{1A}$ agonists may also be antidepressants. Since the postsynaptic $5\text{-HT}_{1A}$ receptor may be less sensitive than autoreceptor, high doses of $5\text{-HT}_{1A}$ agonists, particularly very effective ones (i.e., those causing greater stimulation of the $5\text{-HT}_{1A}$ receptor, a parameter referred to as "efficacy"), can be expected to be effective anti-depressants. Gepirone has already been demonstrated to have ameliorative effects on some depressive endpoints in some patients.

Serotonin is also involved in the regulation of feeding and sexual behavior and in cardiovascular regulation. Thus, $5\text{-HT}_{1A}$ agonists may be useful in treating overeating and sexual dysfunction. These compounds have been shown to alter feeding and sexual behavior in animals. $5\text{-HT}_{1A}$ agonists are also known to depress sympathetic nerve discharge and thus lower blood pressure. Thus, they may be useful in treating hypertension, congestive heart failure (by reducing cardiovascular afterload) and heart attack (by removing sympathetic drive to the heart).

Schizophrenia is thought to be due to hyperactivity in DA systems. Thus, currently available anti-psychotics are DA antagonists. Dopamine autoreceptors depress DA neuron firing rates, DA synthesis and release. Thus DA autoreceptor agonists can also be expected to be anti-psychotics. DA agonists are also useful for treating Parkinsonism, a disease caused by degeneration of DA neurons, and hyperprolactinemia, since DA agonists depress prolactin release.

Dopamine autoreceptor antagonists are a new class of drug that increase release of DA by releasing the DA neuron from autoreceptor control. Thus, these drugs can be expected to be useful in conditions treatable with amphetamine and other similar stimulants which directly release DA. However, because DA autoreceptor agonists will be much milder stimulants because, rather than directly releasing DA, they simply increase the release associated with the normal DA activity by releasing the cell from autoreceptor control. Thus, DA autoreceptor antagonists can be expected to be useful in treating overeating, attention deficit disorders, psychiatric, cognitive and motor retardation in demented and elderly patients, and in treating nausea and dizziness with space travel.

The compounds of the present invention have a variety of effects at $5\text{-HT}_{1A}$ and DA receptors, and offer a variety of utilities associated with those activities.

The search for new CNS active compounds is focused on finding compounds with selective $5\text{-HT}_{1A}$ receptor agonist effects without detrimentally influencing central dopamine receptors.

Drugs acting on central dopamine transmission are clinically effective in treating a variety of central nervous system disorders such as parkinsonism, schizophrenia, and manic-depressive illness. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical anti-psychotic agents directly block the postsynaptic dopamine receptor. The same effect can be achieved by inhibition of intraneuronal presynaptic events essential for the maintenance of adequate neurotransmission, transport mechanism and transmitter synthesis.

In recent years a large body of pharmacological, biochemical and electrophysical evidence has provided considerable support in favor of the existence of a specific population of central autoregulatory dopamine receptors located in the dopaminergic neuron itself. These receptors are part of a homeostatic mechanism that modulates nerve impulse flow and transmitter synthesis and regulates the amount of dopamine released from the nerve endings.

Direct dopamine receptor agonists, like apomorphine, are able to activate the dopamine autoreceptors as well as the post synaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The anti-psychotic and anti-dyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

The following documents could be important in the examination of this application.

Arvidsson, L.-E., et at., J. Med. Chem., 24, 921 (1981), describes hydroxy-2-aminotetralins where the amine is substituted with one n-propyl, one benzyl or two n-propyl substitutents. The 5-, 6-, and 7-hydroxy compounds are described as active central dopamine-receptor agonists and the 8-hydroxy compound is described as a central 5-HT receptor agonist devoid of dopamine receptor stimulating activity.

Arvidsson, L.-E., et al., J. Med. Chem., 27, 45 (1984), describes 2-aminotetralins where the amine is substituted with one or two methyl, ethyl, n-propyl, i-propyl, n-butyl, or benzyl substituents. The 2-piperidinyltetralin is also described. Several of these compounds were found to be potent 5-HT agonists devoid of dopamine-mimetic effects.

Arvidsson, L.-E., et al., J. Med. Chem., 30, 2105 (1987), describes 8-hydroxy- 1-methyl-2-(di-n-propylamino)tetralins. These compounds were 5-HT receptor agonists.

The Arvidsson, L.-E., et al 8-hydroxy and 8-methoxy tetralin compounds are also disclosed in Derwent documents 00389J/47, 94981D/51 and 045535J.48.

McDermed, et al., J. Med. Chem., 18, 362 (1975) describes 5,6-dihydroxy-2-aminotetralins. In addition, the 5,8 and 7,8 disubstituted compounds are also disclosed. The amine can be a mono or di substituted with simple alkyl groups, benzyl groups alkylalkoxy groups or the amine can be a 5 or 6 membered hydrocarbon or heterocyclic amine. These compounds are indicated to have dopaminergic properties although certain compounds are reported to be inactive.

McDermed, et al., J. Med. Chem., 19, 547 (1976) describes 5-, 6-, or 7-hydroxy- 2-dipropylaminotetralins. These compounds are described as dopaminergic compounds.

Rusterholz, et at., J. Med. Chem., 19, 99 (1976) describes 5,8 disubstituted-2-aminotetralins with the amine being substituted with hydrogen, methyl, or cyanopropyl groups. Some of these compounds are potent prolactin inhibitors and believed to be dopamine agonists.

Ames, et al., J. Chem. Soc. 2636 (1965) describes the preparation of a large number of compounds, where the aromatic ring is substituted by methoxy, ethoxy, n- or iso-propoxy, or n-, sec- or tert-butoxy group in the 5 or 8 position and the amine is substituted by hydrogen or alkyl groups having 1-4 carbon atoms. The compounds are indicated to be prepared for pharmacological testing. However, no utility or pharmacological activity is yet known for the compounds just mentioned.

German Patent DE-A1-2 803 582 describes 2-aminotetralins where the aromatic ring is substituted on the 5,6,7 or 8 position with the group $R_1$, where $R_1$ is hydrogen, alkanoyl having 1 to 20 carbon atoms or a group —CO—$(CH_2)_n$—$R_7$, n is a number 0 to 5, $R_7$ is a phenyl group with substituents as defined further, $R_2$ is hydrogen, hydroxy, halogen or alkylsulfonylamino, $R_3$ is hydrogen, $R_4$ is hydrogen, $CH_2OH$, $CH_2O$—CO—$R_8$ or $CH_2$—O—CO—$(CH_2)_n$—$R_7$ with further definition and $R_5$ and $R_6$ are hydrogen, alkyl or aryl or aralkyl groups further defined or $R_5$ and $R_6$ are together an alkylene with 4 to carbon atoms. The compounds are disclosed as having pharmacodynamic activity in particular a stimulating effect on alpha-and beta-adrenoceptors and dopamine receptors. Among the compounds described are compounds having the group $R_{10}$ in the 8 position and having $R_2$ or $R_4$ other than hydrogen.

Great Britain Patent 1,377,356 describes 2-aminotetralins where the aromatic ring is substituted on the 5, 6,7 or 8 position by $R_1$, where $R_1$ is hydrogen or methyl, the aliphatic ring is substituted by $R_2$, where $R_2$ is alkyl having 1–6 carbon atoms, and the amine is substituted by $R_3$, where $R_3$ is hydrogen or alkyl having 1–6 carbon atoms are described. Such compounds are stated to possess analgesic activity. 1,1-Dimethyl-2-(N,N-dimethylamino)- 7-hydroxytetralin is mentioned as one example of a compound covered by the patent. This compound is also described in Chem. Ab., 79: 146294b as having analgesic and intestinal movement accelerating actions.

J. Pharm. Sci., 67, 880–82 (1978)describes the compound 1-methyl-2-(cyclopropylamino)- 5-methoxytetralin and indicates the compound possess local anesthetic activity.

Derwent documents 58,247B/32, 40 378A/23, 83–729388/32, 83–72987/32, 29348D/17 and 06733V/05 refer to 8-carboxyamino tetralins. Additional 07833V/05 refers to 8-amido and 8-alkylamido tetralin.

EPO patent application EPO 270 947 (1988) discloses 8-hydroxy and 8-methoxytetralins.

EPO patent application EPO 0 272 534 (1988) discloses aminotetralins including 8-amido compounds.

The references cited herein are disclosures describing work related to the invention:

Hjorth, S.; Carlsson, A; Lindberg, P.; Sanchez, D.; Wikstron, H.; Arvidsson, L.-E.; Hacksell, U.; Nilsson, J. L. G., *J. Neural Transm.*, 1982, 55, page 169.

Mellin, C.; Bjork, L.; Karlen, A.; Johansson, A. M.; Sundell, S.; Kenne, L.; Nelson, D. L.; Anden, N.-E.; Hacksell, U., *J. Med, Chem.*, 1988, 31, page 1130.

Cossery, J. M.; Gozlan, H.; Spampinato, U.; Perdicakis, C.; Guillaumet, G.: Pichat, L.; Hamon, M., *European J. Pharmacol.*, 1987, pages 140, 143.

INFORMATION DISCLOSURE STATEMENT

Trans-7- and trans-9-hydroxy-1,2,3,4,4a,5,6,10b-octahydrobenzo [P]quinolines have been synthesized and their effects on central dopamine and α-receptors have been studied. Arvidsson, L.-E. et al, *J. Med, Chem*, 1983, 27, page 45.

Octahydrobenzo-isoquinolines are also described in Derwent 84-073373/13.

Hexahydrobenzo-isoquinolines are described in Derwent 55370A/31 (DT 2801 576).

Derwent 83-840180/50 and 86-298374/45 discloses tetrahydro-benzo-isindoline derivatives which interact specifically with various androgenic receptors and are useful for treating hypertension. 86-298374/45 also discloses that the compounds also have sedative activity.

French patent 1,555.553 (Derwent 372 16 describes 2,3, 4,4a,5,6-hexahydrobenzo(f)quinolines.

U.S. Pat. No. 4,622,405 discloses 1,2,3,3α,8,8a-hexahydro indero(1,2-C)pyrroles(s).

Derwent 63503T-B, 52201R-B, 23543R, 30016 and 41102 disclose hexahydroinenopyridinols.

Derwent 67323W/41 discloses benzoisoindolines as antiagressive and analgesic agents.

SUMMARY OF THE INVENTION

This invention encompasses compounds of Formula I, where Y is hydrogen or halogen wherein $R_1$ is
  (a) -hydrogen
  (b) —$OR_4$ (c) —SR$_4$
(d) —OSO$_2$CF$_3$
(e) —CONR$_6$R$_6$
(f) —CO—(2-pyrrolyl)

wherein A is Formula a or Formula b,
wherein R$_2$ is
(a) -hydrogen
(b) —(C$_1$–C$_8$)alkyl
(c) —(C$_3$–C$_8$)alkenyl
(d) —(C$_3$–C$_8$)alkynyl
(e) —(CH$_2$)$_m$-(C$_3$–C$_8$)cycloalkyl
(f) —(CH$_2$)$_m$—(C$_3$–C$_8$)cycloalkenyl
(j) —(CH$_2$)$_m$-aryl
(h) —(CH$_2$)$_m$-CO$_2$R$_6$ wherein R$_3$ is
(a) -hydrogen
(b) —(C$_1$–C$_4$)alkyl
(c) -aryl
(d) —(CH$_2$)$_n$—CO—(C$_1$–C$_4$)alkyl
(e) —CO—aryl wherein R$_4$ and R$_5$ are
(a) -hydrogen
(b) —(C$_1$–C$_4$)-alkyl
(c) —(C$_2$–C$_4$)alkenyl
(d) -aryl wherein R$_6$ is
(a) -hydrogen
(b) —(C$_1$–C$_4$)alkyl
(c) -aryl wherein
m is 1–4
n is 0–3.

The compounds of this invention possess selective pharmacological properties and are useful in treating central nervous system disorders including anti-depression symptoms, anxiolytic symptoms, panic attacks, obsessive-compulsive disturbances, senile dementia, emotional disturbances related to dementia disorders, and stimulation of sexual activity. The compounds of this invention are also useful to alleviate aggressive behavior, confusional delirious states and impotence. In addition to their central nervous system pharmacological activities, the compounds of this invention are also anti-diabetic, anti-obesity, anti-atherosclerotic, and anti-hypertensive agents. Processes for preparation of these compounds, their pharmaceutical use and pharmaceutical preparations employing such compounds constitute further aspects of the invention.

According to a preferred embodiment the invention is related to compounds of Formula I. For example, cis-(±)-2,3,3a,4,5,9b-hexahydro-6-methoxy-3-(2-propenyl)-1H-benz[e]indole hydrochloride exhibits good selective dopamine activity.

An object of the invention is to provide compounds for therapeutic use, especially compounds having a therapeutic activity in the central nervous system. Another object is to provide compounds having an effect on the 5-HT$_{1A}$ receptor in mammals including man. A further object of this invention is to provide compounds having an effect on the subclass of dopamine receptors known as the D$_2$ receptor.

DETAILED DESCRIPTION OF THE INVENTION

The compounds of this invention are identified in two ways: by the descriptive name and reference to labelled structures contained in appropriate charts. In appropriate situations, the proper stereochemistry is also represented in the charts.

In this document the parenthetical term (C$_n$–C$_m$) is inclusive such that a compound of (C$_1$–C$_8$) would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl.

Alkoxy as represented by —OR$_1$ when R$_1$ is (C$_1$–C$_8$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, isohexoxy, n-heptoxy, isoheptoxy, and n-octoxy.

Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl. Cycloalkyl refers to a radical of a saturated cyclic hydrocarbon such as cyclopropyl, cyclobutyl, cyclopentyl, cyclohexyl, cycloheptyl, or cyclooctyl.

LDA is lithium diisopropyl amide.

It will be apparent to those skilled in the art that compounds of this invention may contain chiral centers. The scope of this invention includes all enantiomeric or diastereomeric forms of Formula I compounds either in pure form or as mixtures of enantiomers or diastereomers. The compounds of Formula I contain two asymmetric carbon atoms in the aliphatic ring moiety, including the ring carbon atoms adjacent to the nitrogen atom. The therapeutic properties of the compounds may to a greater or lesser degree depend on the stereochemistry of a particular compound. Pure enantiomers as well as enantiomeric or diastereomeric mixtures are within the scope of the invention.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, palmoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and outlined in the appropriate charts.

The (1,2N) carbocyclic 2-aminotetralins of this invention can be made in accordance with the processes illustrated in Charts A, B and C and the (3,2N) compound can be made in accordance with the process illustrated in Charts D, E, and F.

Chart A

In step 1, 2-tetralone (A-1) is reacted with allylbromide in the presence of LDA and tetrahydrofuran to provide A-2.

A-2 is then subjected to reductive amination by reacting it with the appropriate amine in the presence of NaBH$_3$CN, acetic acid, tetrahydrofuran and methyl alcohol to yield compound A-3. A$_3$ is first reacted with mercuric acetate and methanol and the resulting compound is subjected to reduction by sodium borohydride in sodium hydroxide to yield compound A-4. A-4 is O-demethylated via methods known in the art to yield A-5.

Chart B

In step 1 of method B, 2-tetralone (B-1) is reacted with an appropriate bromoester in the presence of LDA and tetrahydrofuran to provide B-2. In step 2, B-2 is subjected to the same reductive amination step as in step 2 in Method A to yield B-3. In step 3, B-3 is subjected to reduction to yield B-4. B-4 is O-demethylated via methods known in the art to yield B-5.

Chart C

In step 1, 2-tetralone (C-1) is reacted with dimethylcarbonate in the presence of base to give 1-carbomethoxy substituted tetralone derivative C-2. In step 2, C-2 is subjected to the same reductive amination step as in step 2 in Method A to yield C-3. In step 3, C-3 is subjected to lithium aluminum hydride to yield C-4. C-4 was treated with p-toluene sulfonyl chloride and pyridine resulting in conversion to C-5.

Chart D

In step 1, tetralone derivative Do 1 is subjected to the same step as in step 1 in method C to give substituted tetralone derivative D-2. Allylation in the presence of base in step 2 gives 1-carbomethoxy-3-allyl derivative D-3. Decarboxylation in step 3 gives 3-allyl-tetralone derivative D-4. Reductive amination in step 4 gives aminotetraline derivative D-5. Amino-mercuration in step 5 gives 3,2N tricyclic derivative D-6.

Chart E

In step 1, the keto group in 3-allyltetralone derivative E-1 (D-4) is protected to form ketal derivative E-2. Oxidation of the allyl group of E-2 to an acid followed by esterification in step 2 gives a 3-allyl-2-keto-ester derivative E-3. Reductive amination followed by lithium aluminum hydride reduction in step 3 gives the 3,2N tricyclic derivative E-4.

Chart F

In step 1, ketal derivative F-1 (E-2) is hydroborated to form alcohol F-2. F-2 is in step 2 oxidized, hydrolyzed and esterified to give keto-ester F-3. Reductive amination followed by lithium aluminum hydride reduction in step 3 gives the 3,2N-tricyclic derivative F-4.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutical treatment the suitable daily doses of the compounds of the invention are 1–2000 mg/kg for oral application, preferentially 50–500 mg, and 01–100 mg for parenteral application, preferentially 0.5–50 mg.

The compounds of this invention where R$_1$ is in 8-position in the aromatic ring are very selective 5-HT$_{1A}$ receptor agonists having generally little or no dopaminergic activity. The IC50 ratio of dopamine D$_2$ to 5-HT$_{1A}$ in vitro binding data shown in Table I for one compound of this invention, (Example 4, compound #2) demonstrates the selectivity for the 5-HT$_{1A}$ receptor. The compound of this invention where R$_1$ is in 5-position in the aromatic ring, on the other hand, have dopaminergic activity with little 5-HT$_{1A}$ agonist activity. The data shown in Table I for one compound of this invention, (Example 4, compound #3) demonstrates low 5-HT$_{1A}$ agonist activity yet showing a selective dopamine antagonist activity based on evaluation of dopamine and serotonin metabolites. These compounds are particularly effective anxiolytic and antidepressant agents. Other uses for these compounds include panic attacks, obsessive-compulsive disturbances, and senile dementia particularly the emotional disturbances seen in dementia disorders. In addition, central 5-HT receptor activation are believed to be involved in mediating sexual behavior. These compounds would be useful to stimulate sexual activity and to alleviate impotence. The compounds of this invention are also useful to alleviate aggressive behavior, confusional delirious states.

The compounds of this invention also have been shown to have high oral potency and a long duration of action. Both these features are beneficial to effective clinical treatment.

The utility of the compounds of this invention to treat central nervous system disorders is shown in behavioral, physiological and biochemical tests. The methods are given as follows:

Binding: Inhibition of 8-OH-DPAT binding in a bovine brain homogenate. Potency is given as nM dose required to inhibit 50% of DPAT binding (IC50). This test measures ability to bind to 5-hydroxytryptamine (5-HT$_{1A}$) receptor.

Hypothermia: Starting with a dose of 30 mg/kg, four mice are injected subcutaneously with test compound. Twenty minutes later, the number of animals whose body temperature has decreased by 2° C. or more are counted. If all four animals reach criteria, the drug is considered "active", and subsequent readings are taken at 60 and 120 minutes after drug. The time for last statistically significant drug affect on mean body temperature is indicated in minutes. For all "active" compounds, doses are lowered by 0.5 log intervals until a dose which does not lower body temperature by 2° C. in any animal is found. Potency is given as mg/kg ED50 (dose required to depress temperature in two of four mice) as measured by Spearman-Karber statistics.

Sympathetic Nerve Discharge (SND): The i.v. mg/kg dose causing a 50% depression in SND in chloralose anesthetized cats and the maximum inhibition of sympathetic activity observed in the dose range tested (0.00 1–1.0 mg/kg i.v. ).

BP SND/MAX: The blood pressure of the chloralose anesthetized cats in percent control at the dose causing 50% depression in SND and the maximum reduction in blood pressure as percent of the control blood pressure in the same animals observed in the dose range tested (0.001–1.0 mg/kg i.v.).

CNS and anti-hypertensive biological data are shown in Tables I and II respectively.

TABLE I

CNS BIOLOGICAL DATA

| Example No. (Compound Number) | 5-HT$_{1A}$ Binding IC$_{50}$ (nM) | Hypothermia ED$_{50}$ (mg/kg) |
|---|---|---|
| 2 Compound #1 | 0.96 | 5.5 |
| 4 Compound #2 | 2.8 | 2.3 |
| 4 Compound #3 | 627.9 | 30.0 |
| 5 Compound #1 | 14.8 | 4.1 |

TABLE II

ANTI-HYPERTENSIVE BIOLOGICAL DATA

Serotonin SND Assay

| Example No. (Compound Number) | SND ED$_{50}$ (mg/kg) | Max. Decr. SND % | % BP Control | Max. Decr. BP (at SND ED50) |
|---|---|---|---|---|
| 4 Compound #1 | 0.09 | 0.0 | 76 | 60 |
| 5 Compound #1 | 0.083 | 14.0 | 77 | 59 |

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

1,2,3,4-Tetrahydro-2-oxo-1-(2-propenyl)-naphthalene 1,2,3,4-tetrahydro-
2-oxo-1,1,di-(2-propenyl)naphthalene (A-2, Chart A)

To a solution of 7.3 g (50 mmol) 2-tetralone in 75 ml THF in a three-neck round-bottomed flask, equipped with a gas inlet and septum, was added 36.7 mL LDA (55 mmol, 1.5M in cyclohexane, at −30° C. under a nitrogen atmosphere. The solution was allowed to warm to 0° C. over a thirty-minute period and 5.6 mL (65 mmol) ethyl bromide was added. TLC analysis was used to monitor the reaction. After stirring for 24 hours at room temperature, the reaction mixture was quenched with 10% sodium bisulfate to pH2-3. After removal of THF under reduced pressure, the mixture was extracted with ethyl acetate (2×1 L) and the combined organic layers were washed with brine, dried (MgSO$_4$), filtered and concentrated in vacuo. The crude product was purified by liquid chromatography on 800 g of silica gel 60 (230–400 m), eluting with 1 L hexane, followed by 5 L of 5% ethyl acetate/hexane, and collecting 40 mL fractions. Fractions 41–64 gave 4.2 g (37%) of pure and 1,2,3,4-tetrahydro-2-oxo-1,1-di-(2-propenyl)naphthalene as a colorless oil and fractions 65–82 gave 3.1 g (33%) of pure 1,2,3,4-tetrahydro-2-oxo-1-(2-propenyl)-naphthalene as a light yellow oil.

$^1$HNMR (CDCl$^3$, TMS): δ7.27–7.16 (m, 4H); 5.81–4.95 (m, 3H); (s, 3H); 3.54– 2.45 (m, 7H).

IR film: ñ$_{max}$ 1717, 1640 and 1582 cm$^{-1}$.

MS: M$^+$ 186, other ions at m/z 168, 145, 128 and 117.

TLC (silica gel GF): R$_f$=0.51 hexane/ethyl acetate (4:1).

Utilizing a similar procedure as in Preparation 1 but using the appropriate starting material, there is obtained 1,2,3,4-tetrahydro-8-methoxy-2-oxo-2-(2-propenyl) naphthalene.

1HNMR (CDCl$_3$, TMS) δ7.21–6.76 (m, 3H); 5.73–4.87 (m, 3H); 3.82 (s, 3H); 3.88–382 (m, 1H); 3.32–2.43 (m. 6h).

IR (film): ñ$_{max}$ 1712, 1640, 1586 cm$^{-1}$.

MS: Calcd for C$_{14}$H$_{16}$O$_2$: 216.1150. Found: 216.1151.

Analysis: Calcd for C$_{14}$H$_{16}$O$_2$: C, 77.75; H, 7.46. Found: C, 77.56; H, 7.68.

TLC (Silica Gel GF): Rf=0.32 in hexane/acetone (4:1).

Preparation 2 trans-(+−)-3,4.4a,5,10,10a-hexahydro-9-methoxy-1-
(2-propenyl-2(1H)benzo[ g]quinolin-2-one as A and
cis-(+−)-3,4,4a,5,10–10a-hexahydro-9-methoxy-1-(2
-propenyl)-2(1H)-benzo[g]-quinolin-2-one as
B.(B-3, Chart B)

To a solution of 2.2 g (8.4 mmol) of (+−)-1,2,3,4-tetrahydro-5-methoxy-4-oxo-2 -naphthalene-propanoic acid methyl ester (preparation 7) and 2.5 mL (33.6 mmol) of allylamine in 42 mL methanol/THF (1:1) was treated with acetic acid (ca 6.7 mL) at 0°– 5° C. until the pH of the mixture was 4–5. The mixture was stirred for 30 minutes and 1.06 g (16.8 mmol) of sodium cyanoborohydride was added. The resulting solution was stirred at room temperature for five days. The reaction was then quenched with 20% sodium hydroxide and concentrated in vacuo. The concentrate was extracted with methylene chloride (2×1 L) . The organic layer was washed with brine, dried (MgSO$_4$), filtered and concentrated in vacuo. The crude product was purified by liquid chromatography on 400 g of silica gel 60 (230–400 m), eluting with hexane-acetone (4: 1) and collecting 40 mL fractions. Fractions homogeneous by TLC were combined and concentrated in vacuo. Fractions 101–108 gave 0.26 g (11.6%) of pure A as a white solid after recrystallization from hexane/ethyl acetate: top. 104°–105° C. Fractions 110–138 afforded 1.8 g (79%) of pure B as a white solid after recrystallization from hexane/ethyl acetate: mp. 71°–72° C.

Trans-(+−)-3,4,4a,5,10-10a-hexahydro-9-methoxy-1-(2-propenyl)-2(1H)benzo[ g]quinolin-2-one (A).

$^1$HNMR (CDCl$_3$, TMS): 7.14–6.14 (m, 3H); 5.88–5.16 (m, 3H); 3.83 (s, 3H); 4.65–1.52 (m, 12H).

IR (mull): ñ$_{max}$ 1652, 1637, 1602 and 1585 cm$^{-1}$.

MS: M$^+$ 271, other ions at m/z 271,256, 214, 186, 172, 159, 144, 134.

Analysis: Calcd for C$_{17}$H$_{21}$NO$_2$: C, 75.24; H, 7.80; N, 5.16. Found: C, 75.36; H, 8.09; N, 5.21.

Cis-(+−)3,4,4a,5,10,
10a-hexahydro-9-methoxy-1-(2-propenyl)-2(1H)-
benzo[g]quinolin- 2-one $^1$HNMR (CDCl$_3$, TMS): 7.14–6.14 (m, 3H); 5.88–5.16 (m, 3H); 3.83 (s, 3H); 4.72–1.58 (m, 12H).

IR (mull): ñ$_{max}$ 1644, 1627, 1601 and 1587 cm$^{-1}$.

MS: M$^+$ 271, other ions at m/z 256, 214, 186, 172, 159, 144, 134.

Analysis: Calcd for C$_{17}$H$_{21}$NO$_2$: C, 75.24; H, 7.80; N, 5.16. Found: C, 75.36; H, 8.09; N, 5.21.

Utilizing a procedure similar to Preparation 2, using the appropriate starting material and substrate, there is obtained cis-1,3,3a.4,5,9b-hexahydro-3-(2 -propenyl)-2H-benz[e]-indol-2-one as a yellow oil.

$^1$HNMR (CDCl$_3$, TMS): δ7.2–7.0 (m, 4H); 5.80–5.20 (m, 3H); 4.40 (m, 1H); 3.90 (m, 1H); 3.60 (m, 2H); 2.90 (m, 1H); 2.80–2.60 (m, 2H); 2.35 (t, 1H); 2.05 (m, 1H); 1.7 (m, 1H).

TLC (Silica Gel GF): Rf=0.29 in hexane-acetone (4:1).

cis-(+–)-1,3,3a,4,5,9b-hexahydro-9-methoxy-3-(2-propenyl)-2H-benz[e]indol-2one as a colorless oil.

$^1$HNMR (CDCl$_3$, TMS): δ7.12–6.72 (m, 3H); 5.87–5.22 (m, 3H); 4.10–4.36 (d of d, 1H); 3.81 (s 3H); 3.72–1.68 (m, 9H).

IR (mull): ñ$_{max}$ 3580, 3442, 1680, 1598 and 1572 cm$^{-1}$.

MS: Calcd for C$_{16}$H$_{19}$NO$_2$: 257.1416. Found: 257.1414.

Analysis: Calcd for C$_{16}$H$_{19}$NO$_2$: C, 74.68; H, 7.44; N, 5.44. Found: C, 73.02; H, 7.70; N, 5.32.

Cis-(+–)-1,3,3a,4,5,9b-hexahydro-6-methoxy-3-(2-propenyl)-2H-benz[e]indol-2-one as a white solid: mp. 89°–90° C.

$^1$HNMR (CDCl$_3$, TMS): δ7.19–6.69 (m, 3H); 5.38–5.20 (m, 3H); 4.45–4.34(m, 1H); 3.82 (s 3H); 3.94–1.54 (m, 9H).

IR (mull): ñ$_{max}$ 1684 and 1641 cm$^{-1}$.

MS: M$^+$ 257, other ions at m/z 242, 228, 172, 158.

Analysis: Calcd for C$_{16}$H$_{19}$NO$_2$: C, 74.68; H, 7.44; N, 5.40. Found: C, 74.40; H, 7.46; N, 5.60.

trans-(+–)-1,3,3a,4,5,9b-hexahydro-6-methoxy-3-(2-propenyl)-2H-benz[e]indol-2-one recrystallized from hexane/ethyl acetate to give a white solid: mp. 137°–138° C.

$^1$HNMR (CDCl$_3$, TMS): δ7.20–6.64 (m, 3H); 5.88–5.14 (m, 3H); 4.22–4.14 (d of d, 1H); 3.82 (s, 3H); 3.83–1.60 (m, 9H).

IR (mull): ñ$_{max}$ 1686, 1603, and 1582 cm$^{-1}$.

MS: M$^+$ 257, other ions at m/z 242, 228, 173.

Analysis: Calcd for C$_{16}$H$_{19}$NO$_2$: C, 74.68; H, 7.44; N, 5.44. Found: C, 74.74; H, 7.72; N, 5.44.

Cis-(+–)-1,3,3a,4,5,9b-hexahydro-9-methoxy-3-(2-propyl)-2H-benz[e]indol-2-one as a yellow oil $^1$HNMR (CDCl$_3$, TMS): δ7.15–6.70 (m, 3H); 3.81 (s 3H); 3.79–1.50 (m, 12H); 0.94 (t, 3H).

MS: M$^+$ 259, other ions at m/z 244, 230, 216, 202, 188, 173.

TLC (Silica Gel GF): Rf=0.47 in hexane-ethyl acetate (3:1).

Cis-(+–)-1,4,4a,4,5,6,10b-hexahydro-10-methoxy-4-(2-propenyl)-benz[f]quinolin-( 3(2H)-one as an oil.

HNMR (CDCl$_3$, TMS): 7.13–6.69 (m, 3H); 5.83–5.13 (m, 3H); 4.64–4.59 (d of d, 1H); 3.83 (s 3H); 3.60–1.73 (m, 11H).

TLC (Silica Gel Gf): Rf=0.33 in hexane-acetone (2:1, 5% 2-cis- 1,2,3,4-tetrahydro-8-methoxy-2-(2-propenylamino)-1-naphthalenecarboxylicacid methyl acid methyl ester.(C-3, Chart C)

$^1$HNMR (CDCl$_3$, TMS): δ7.25–6.78 (m, 3H); 6.01–5.51 (m, 3H); 3.81 (s, 3H); 3.71 (s, 3H); 4.46–1.82 (m, 9H).

IR mull: ñmax 1731, 1604 and 1579 cm$^{-1}$.

MS Calcd for C$_{16}$H$_{21}$NO$_3$: 275.1521. Found: 275.1535.

Analysis calcd for C$_{16}$H$_{21}$NO$_3$.HCl: C, 61.63; H, 7.11; N, 4.49. Found: C, 61.98; H, 7.34; N. 4.73.

TLC (Silica Gel Gf): Rf=0.26 in hexane ethyl acetate (1:1).

Preparation 3

1,2,3,4-Tetrahydro-2-oxo-1-naphthalene acetic acid methyl ester (B-2, Chart B)

A three-neck, round-bottomed flask equipped with a dropping funnel and a septum, was charged with 6.6 mL (50 mmol) of beta-tetralone and 100 mL of THF under a nitrogen atmosphere. The solution was cooled to −30° C. and 36.6 mL (55 mmol) of LDA (1.5M in cyclohexane) was added dropwise. The solution was stirred for 30 minutes and warmed to 0° C. To this solution, 5.7 mL (60 mmol) of methyl bromoacetate was added. The solution was stirred at 0° C. for 1 h. The reaction was quenched with 3N HCl until pH of the mixture was <3. THF was removed in vacuo and the concentrate was extracted with methylene chloride (2×500 mL). The organic layer was washed with brine, dried (MgSO$_4$), filtered and concentrated in vacuo to give a yellow oil. This oil was purified by liquid chromatography on 560 g silica gel 60 (230°–400 m), eluting with hexane-ethyl acetate (4:1) and collecting 40 mL fractions. Fractions homogeneous by TLC were combined and concentrated in vacuo. The resulting oil needed the second chromatography to afford 8.22 g (75.4%) of >95% pure product as a near colorless oil.

$^1$HNMR (CDCl$_3$, TMS): δ7.28–7.09 (m, 4H); 3.98–3.94 (t, 1H); 3.68 (s, 3H); 3.58–2.42 (m, 6H).

TLC (Silica Gel GF): Rf=0.25 in hexane-acetone (4:1).

Utilizing a procedure similar to that of Preparation 3 but using the appropriate starting materials there is obtained (+–)-1,2,3,4-tetrahydro-8-methoxy-2-oxo-1-naphthaleneacetic acid methyl ester.

$^1$HNMR (CDCl$_3$, TMS): 7.19–6.78 (m, 3H); 3.83 (s, 3H); 3.81 (m, 1H); 3.56 (s, 3H); 3.29–2.57 (m, 6H).

IR (film): $_{max}$ 1741, 1713, 1601, and 1587 cm$^{-1}$.

MS: Calcd for C$_{14}$H$_{16}$O$_4$: 248.1048. Found: 248.1049.

Analysis: Calcd for C$_{14}$H$_{16}$O$_4$: C, 67.72; H, 6.49. Found: C, 67.60; H, 6.60.

(+–)-1,2,3,4-Tetrahydro-5-methoxy-2-oxo-1-naphthaleneacetic acid methyl ester $^1$HNMR (CDCl$_3$, TMS): δ7.23–6.72 (m, 3H); 3.94 (t, 1H); 3.85 (s, 3H); 3.68 (s, 3H); 3.32–2.42 (m, 6H).

IR (film): ñ$_{max}$ 1729, 1717, 1686, 1676, 1600 and 1588 cm$^{-1}$.

MS: M$^+$ at 248, other ions at m/z 217, 216, 188, 174.

Analysis: Calcd for C$_{14}$H$_{16}$O$_4$: C, 67.73; H, 6.50. Found: C, 67.73; H, 6.73.

1,2,3,4-Tetrahydro-8-methoxy-2-oxo-1-naphthalenecarboxylic acid methyl ester. (D-2, Chart D)

$^1$HNMR (CDCl$_3$, TMS): δ7.23–6.72 (m, 3H); 4.72 (s, 1H); 3.80 (s, 3H); 3.72– 2.17 (m, 7H).

IR (film): ñ$_{max}$ 1750, 1718 and 1588 cm$^{-1}$.

MS: M$^+$ at 234, other ions at m/z 202, 191,174, 147, 131,115, 103, 91.

Analysis: Calcd for $C_{13}H_{14}O_4$: C, 66.65; H. 6.02. Found: C, 66.49; H, 5.93.

TLC (Silica Gel GF): Rf=0.33 in hexane/ethyl acetate (3:1).

Preparation 4

(+−)-3',4'-Dihydro-8'-methoxy-3'-(2-propenyl)-spiro-(1,3-dioxolane- 2,2'[1'H]naphthalene.(E-2, Chart E)

A solution of 1,2,3,4-tetrahydro-8-methoxy-3-(2-propenyl)-2-oxo-naphthalene(15 g, 68 mmol), 30 mL (272 mmol) trimethyl orthoformate, 38 mL (680 mmol) ethylene glycol, 0.13 g (0.68 mmol) p-toluenesulfonic acid monohydrate, and 306 mL methylene chloride was stirred at room temperature under a nitrogen atmosphere for 24 hours. TLC analysis showed no starting material remaining. The reaction was quenched with saturated sodium bicarbonate and extracted with methylene chloride (2×1 L). The organic layer was washed with brine, dried ($MgSO_4$), filtered and concentrated in vacuo to give a yellow oil. This oil was purified by flash chromatography on 1 Kg of silica gel 60 (230–400 m), eluting with 2 L hexane and 5 L hexane-ethyl acetate (9:1) and collecting 500 mL fractions. Fractions 11–14 afforded 15.5 g (88%) as a light yellow oil.

$^1$HNMR (CDCl$_3$, TMS): 7.12–6.64 (m, 3H); 5.90–5.50 (m, 3H); 4.13–3.92 (m, 4H); 3.80 (s, 3H); 3.06–1.84 (m, 7H).

IR(mull): $_{max}$ 1640, 1604 and 1587 cm$^{-1}$.

MS: M$^+$ 260, other ions at m/z 245,219, 206, 174, 160, 147, 134.

Analysis: Calcd for $C_{16}H_{20}O_3$: C, 73.82; H, 7.74. Found: C, 73.48, H, 8.07.

Preparation 5

(+−)-1,2,3,4-Tetrahydro-5-methoxy-3-oxo-2-naphthalene-acetic acid methyl ester (E-3, Chart E)

A three-neck, round-bottomed flask, equipped with a mechanical stirrer and a gas inlet, was charged with 57.8 g (270 mmol) of sodium periodate and 1 L of water under a nitrogen atmosphere. The mixture was stirred for 10 minutes and 2.8 g (18 mmol) of potassium permanganate was added. The resulting purple colored mixture was stirred at room temperature for 30 minutes. Potassium carbonate powder (7.5 g, 54 mmol) was then added and the mixture was stirred for 15 minutes. To this mixture 300 mL of t-butanol (distilled) as added over a period of 10 minutes while the temperature of the mixture was maintained at <30° C. A solution of 7.8 g (30 mmol) 3',4'-dihydro-8'-methoxy-3-2(propenyl)-spiro[1,3-dioxolane-2,2'(1'H)-naphthalene in 300 mL t-butanol was then added over a period of five minutes. The color of the mixture immediately turned from purple to pink. After the mixture was stirred for three hours, TLC analysis showed no starting material remaining (the aliquot was treated with a few drops of aqueous sodium bisulfite and extracted with ethyl acetate). The mixture was cooled to 0°–5° C. and sodium bisulfite powder was added slowly until the pink-brown suspension became clear yellow solution. The mixture was diluted with 1 L water (pH <3) and extracted with 2×2 L portions of methylene chloride. The organic layer was washed with water, brine, dried ($Na_2SO_4$, not $MgSO_4$), filtered and concentrated in vacuo to give 7.3 g of pale yellow solid, appeared to be the ketal-acid. This solid was dissolved in 150 mL acetonitrile and 150 mL HCl/MeOH (prepared by adding 24 mL acetyl chloride to 126 mL of methanol at 0°–5° C.). The yellow solution was allowed to stand in the refrigerator overnight. The mixture was then stirred at room temperature for 3 hours, TLC analysis showed the esterification was completed. To this solution, 30 mL of water was added and the solution was stirred at room temperature for 24 hours. The solvent was then removed in vacuo and the resulting yellow oil was extracted with 2×1 L of ethyl acetate. The organic layer was washed with brine, dried ($MgSO_4$), filtered, and concentrated in vacuo to give a yellow oil. The oil was purified by flash chromatography on 1 Kg of silica gel 60 (230–400 m), eluting with 8 L 5%, 8 L 10% ethyl acetate/hexane, and collecting 500 mL fractions. Fractions 20–31 afforded 4.28 g (57.5% overall yield) as a pale yellow solid. Recrystallization from ethyl acetate/hexane as a white solid: mp. 73°–74° C.

$^1$HNMR (CDCl$_3$, TMS): δ7.21–6.75 (m, 3H); 3.83 (s, 3H); 3.71 (s, 3H); 3.79– 3.38 (q, 2H), 3.14–2.41 (m, 5H).

IR(mull): $_{max}$ 1742, 1717 and 1586 cm$^{-1}$.

MS: M$^+$ 248, other ions at m/z 230, 216, 199, 188, 174, 159, 146.

Analysis: Calcd for $C_{16}H_{20}O_3$: C, 67.73; H, 6.50. Found: C, 67.54, H, 6.71.

Preparation 6

(+−)-1,2,3,4-Tetrahydro-8-methoxy-2-oxo-1-naphthalene propionic acid methyl ester (B-2, Chart B)

A three-neck, round-bottomed flask, equipped with a dropping funnel and septum, was charged with 1.76 g (10 mmol) of 8-methoxy-2-tetralone and 20 mL of THF under a nitrogen atmosphere. The solution was cooled to −30° C. and 7.5 mL (11 mmol) of LDA (1.5M in cyclohexane) was added dropwise. The solution was stirred for 30 minutes and warmed to 0° C. To this solution, 1.3 mL (12 mmol) of methyl bromopropionate was added. The solution was stirred at room temperature for two hours. The reaction was quenched with 3 N HCl until pH of the mixture was <3. THF was removed in vacuo and the concentrate was extracted with methylene chloride (2× 500 mL). The organic layer was washed with brine, dried ($MgSO_4$), filtered and concentrated in vacuo to give a yellow oil. This oil was purified by liquid chromatography on 400 g silica gel 60 (230–400 m), eluting with hexane-acetone (4:1), and collecting 40 mL fractions. Fractions homogeneous by TLC were combined and concentrated in vacuo to give 1.63 g (63%) of the title compound as a yellow oil.

$^1$HNMR (CDCl$_3$, TMS): δ7.28–6.75 (m, 3H); 3.83 (m, 1H); 3.80 (s, 3H); 3.56 (s, 3H); 3.20–2.05 (m, 8H).

$^{13}$CNMR: 203, 173, 158, 137, 127, 125, 119, 108, 56, 51, 46, 38, 31, 27.5, 27.2.

IR (film): ñ$_{max}$ 1736, 1711 and 1586 cm$^{-1}$.

MS: Calcd for $C_{15}4H_{18}O_6$: 262.1205. Found: 262.1192.

Analysis: Calcd for $C_{15}H_{18}O_4$: C, 68.68; H, 6.92. Found: C, 68.74; H, 7.15.

Preparation 7

(+−)-1,2,3,4-Tetrahydro-5-methoxy-4-oxo-2-naphthalene-propanoic acid methyl ester (F-3, Chart F)

A solution of 6.25 g (24 mmol) 3',4'-dihydro-8'-methoxy-3-(2-propenyl)spiro[ 1,3-dioxolane-2,2'(1'H)-naphthalene in 120 mL THF was cooled to 0°–5° C. under a nitrogen atmosphere. The solution was then treated with 144 mL (72 mmol) of 9-BBN in THF dropwise over a period of 30 minutes. The resulting mixture was stirred at room temperature for three hours. The solution was cooled again to 0°–5° C. and 7 mL water was added. After five minutes, the mixture was treated with 28.8 mL of 3 N sodium hydroxide and was followed by dropwise addition of 28.8 mL addition of 30% hydrogen peroxide. After the mixture was stirred at room temperature for one hour, the mixture was carefully treated with 10% sodium bisulfite to destroy the excess hydrogen peroxide. The mixture was then adjusted to pH 8–9 by adding saturated sodium bicarbonate and extracted with methylene chloride (2×600 mL). The organic layer was washed with brine, dried (MgSO$_4$), filtered and concentrated in vacuo to give a near colorless oil. The oil was purified by LC on 800 g silica gel 60 (230 400 m), eluting with hexane-acetone (2:1), and collecting 40 mL fractions. Fractions 71–105 gave 6.48 g (97%) of pure A as a colorless oil. This oil (6.12 g, 22 mmol) was then dissolved in 220 mL acetone in a three-neck, round-bottomed flask, equipped with a mechanical stirrer, under a nitrogen atmosphere. The solution was cooled to 0°–5° C. and 46.8 mL (125 mmol) of Jones reagent in 93.6 mL acetone was added in five minutes. After the mixture was stirred for 10 minutes, the reaction was quenched with 10% sodium bisulfite until the brown color was converted from brown to green (to destroy the excess reagent). Acetone was removed in vacuo and the residue was extracted with ethyl acetate (2×1 L). The organic layer was washed with brine, dried (Na$_2$SO$_4$, not MgSO$_4$), filtered and concentrated in vacuo to give the carboxylic acid as a brown oil. This oil was dissolved in 110 mL acetonitrile and hydrochloric acid in methanol (prepared by adding 17.6 mL acetyl chloride to 93 mL methanol at 0° C.). The resulting mixture was stirred at room temperature under a nitrogen atmosphere for three hours. The conversion of the carboxylic acid to methyl ester appeared to be completed by TLC. The solution was then treated with 22 mL of water and the mixture was stirred at room temperature under a nitrogen atmosphere for 24 hours (to hydrolyze the ketal). The solvent was removed in vacuo and the residue was extracted with ethyl acetate (2×800 mL). The organic layer was washed with saturated sodium bicarbonate, brine, dried (MgSO$_4$), filtered and concentrated in vacuo. The deep brown oil was purified by LC on 800 g silica gel 60 (230–400 m), eluting with hexane-ethyl acetate (4:1), and collecting 40 mL fractions. Fractions 47–70 afforded 2.35 g (41% overall) of pure B as a light yellow oil.

Physical data for A (F-2, chart F):

$^1$HNMR (CDCl$_3$, TMS): δ7.12–6.64 (m, 3H); 4.10–3.74 (m, 4H); 3.80 (s, 3 H); 3.78–3.63 (m, 2H); 3.38–1.10 (m, 9H).

IR (film): ñ$_{max}$ 3400 and 1587 cm$^{-1}$.

MS: M$^+$ 278, other ions at m/z 247, 233, 219, 206, 189, 175, 161,143.

Analysis: Calcd for C$_{16}$H$_{22}$O$_4$: C, 69.04; H, 7.97. Found: C, 69.14; H, 7.91.

Physical data for B (F-3, chart F):

$^1$HNMR (CDCl$_3$, TMS): δ7.21–6.74 (m, 3H); 3.82 (s, 3H); 3.66 (s, 3H); 3.66–1.26 (m, 9H).

IR (film): $_{max}$ 1737, 1714, 1602 and 1587 cm$^{-1}$.

MS: M$^+$ 262, other ions at m/z 230, 175.

Analysis: Calcd for C$_{15}$H$_{18}$O$_4$: C, 68.68; H, 6.92. Found: C, 68.38; H, 7.01.

Preparation 8 trans-(+−)-1,3,3a.4,9,9b.-Hexahydro-8-methoxy-1-(2-propenyl)-2H-benz[f]indol- 2-one and
cis-(+−)-1,3,3a,4,9-9b-Hexahydro-8-methoxy-1-(2-propenyl)-2H-benz [f]indol-2-one To a solution of 3.97 g (16 mmol) of (+−)-1,2,3,4-Tetrahydro-5-methoxy-3-oxo-2-naphthalene-acetic Acid Methyl Ester and 4.8 mL (64 mmol) of allyl amine in 80 mL MeOH/THF (1:1) was treated with acetic acid (ca 12.8 mL) at 0°–5° C. until the pH of the mixture was 4–5. The mixture was stirred for 30 rain and 2.0 g (32 mmol) of sodium cyanoborohydride was added. The resulting solution was stirred at room temperature for 5 days. The reaction was then quenched with 20% sodium hydroxide and concentrated in vacuo. The concentrate was extracted with methylene chloride (2×1 L). The organic layer was washed with brine, dried (MgSO$_4$), filtered, and concentrated in vacuo. The crude product was purified by liquid chromatography on 800 g of silica gel 60 (230–400 m), eluting with hexane/ethyl acetate/ 2-propanol (10:5: 1) and collecting 40 mL fractions. Fractions homogeneous by TLC were combined and concentrated in vacuo. Fractions 57–61 gave 0.60 g of a yellow oil which was recrystallized from hexane/ethyl acetate to give 0.52 g (13%) of pure trans as a white solid: mp. 102°–104° C. Fractions 94–140 afforded a yellow oil which was recrystallized from hexane/ethyl acetate to give 2.46 g (60%) of pure cis as a white solid: top. 65°–67° C.

Physical data for trans isomer:

$^1$HNMR (CDCl$_3$, TMS: 7.16–6.71 (m, 3H); 5.78–5.17 (m, 3H); 4.38–4.28(m, 1H); 3.84 (s 3H); 3.78–2.08 (m, 9H).

IR (mull): ν$_{max}$ 1683, and 1578 cm$^{-1}$.

MS: M$^+$ 257, other ions at m/z 242,226,214,199,172,158.

Analysis: Calcd for C$_{16}$H$_{19}$NO$_2$: C, 74.68; H, 7.44; N, 5.44. Found: C, 73.79; H, 7.37; N, 5.24.

Physical data for cis isomer:

$^1$HNMR (CDCl$_3$TMS: 7.26–6.75 (m, 3H); 5.81–5.20 (m, 3H); 4.35–4.28 (m, 1H); 3.82 (s, 3H); 3.56–2.0 (m, 9H).

IR (mull):ν$_{max}$ 1641, and 1589 cm$^{-1}$.

MS: M$^+$ 257, other ions at m/z 242,229,213,198,172,158.

Analysis: Calcd for C$_{16}$H$_{19}$NO$_2$: C, 74.68; H, 7.44; N, 5.44. Found: C, 74.61 H, 7.44; N, 5.27.

Utilizing a procedure similar to that of Procedure 8 but using the appropriate starting materials there is afforded:

trans-(+−)-1,3,3a.4,9,9a.-Hexahydro-5-methoxy-1-propyl-2H-benz[f]indol-2-one as a white solid after recrystallization from hexane/ethyl acetate: mp. 121°–123° C.

$^1$HNMR (CDCl$_3$, TMS): 7.19–6.72 (m, 3H); 3.83 (s, 3H); 3.55–1.52 (m, 12H); 0.93 (t, 3H).

IR (mull):ν$_{max}$ 1685, and 1579 cm$^{-1}$.

MS: Calcd for C$_{16}$H$_{21}$NO$_2$: 259.1572. Found: 259.1582.

Analysis: Calcd for C$_{16}$H$_{21}$NO$_2$: C, 74.10; H, 8.16; N, 5.40. Found: C, 74.13; H, 8.50; N, 5.31.

cis-(+−)-1,3,3a,4,9-9a-Hexahydro-5-methoxy-1-propyl-2H-benz [f]indol-2-one as a white solid after recrystallization from hexane/ethyl acetate: mp. 105°–107° C.

$^1$HNMR (CDCl$_3$, TMS): 7.15–6.76 (m, 3H); 3.81 (s, 3H); 3.99–1.45 (m, 12H); 0.92 (t, 3H).

IR (mull): $_{max}$ 1678, and 1588 cm$^{-1}$.

MS: Calcd for C$_{16}$H$_{21}$NO$_2$: 259.1572. Found: 259.1568.

Analysis: Calcd for C$_{16}$H$_{21}$NO$_2$: C, 74.10; H, 8.16; N, 5.40. Found: C, 74.15 H, 8.38; N, 5.40.

EXAMPLE 1

(+−)-2α,3α,4,5,9b,α-hexahydro-2-methyl-3-propyl-1H-benz[e]indole hydrochloride (A-4, Chart A)

A solution of 4.1 g (18 mmol) cis-(+−)-1,2,3,4-tetrahydro-1-(2-propenyl)-N-propyl- 2-naphthalenamine and 17.2 g (54 mmol) of mercuric acetate in 360 mL of methanol was stirred at room temperature under a nitrogen atmosphere for five days. TLC analysis showed no starting material remaining (the aliquot was quenched with small amount of sodium hydroxide/sodium borohydride). The greenish-gray mixture was then treated with a solution containing 2.72 g (72 mmol) sodium borohydride in 20% sodium hydroxide and the resulting mixture was stirred vigorously for three hours. Methanol was removed under reduced pressure and the concentrate was extracted with methylene chloride (2×1 L). The combined organic layers were washed with brine, dried ($MgSO_4$), filtered and concentrated in vacuo. The resulting oil was purified by liquid chromatography on 560 g of silica gel 60 (230–400 m), eluting with hexaneacetone (4: 1), and collecting 40 mL fractions. Fractions 17–23 afforded 2.46 g of the cyclized product as a greenish oil. This oil was repurified again by LC to give 2.0 g (48%) of the desired product as a yellow oil. This oil was converted into HCl-salt by treating with excess HCl/methanol (prepared by adding acetyl chloride to methanol at 0° C.), and recrystallized from ethyl acetate/methanol as a white solid: top. 226°–237° C.

$^1$HNMR ($CDCl_3$, TMS): δ7.20–7.11 (m, 4H); 3.85–1.85 (m, 13H); 1.75 (d, J=7 Hz, 1H); 1.05 (t, J=7Hz, 3H).

IR(mull): $ñ_{max}$ 1603 and 1578 $cm^{-1}$.

MS: Calcd for $C_{16}H_{23}N$: 229.1830. Found: 229.1817.

Analysis: Calcd for $C_{16}H_{23}N.HCl$: C, 72.29; H, 9.10; N, 5.27. Found: C, 72.34, H, 9.13; N, 5.45.

Utilizing a procedure similar to that of Example 1 but using the appropriate starting material there is obtained:

(+−)α,3,3a,α,4,5,9b,α-hexahydro-9-methoxy-2-methyl-3-propyl-1H-benz[e]indole hydrochloride as a white solid top: 177°–178 C.

$^1$HNMR ($CDCl_3$, TMS): δ7.28–6.71 (m, 3H); 3.83 (s, 3H); 3.76–1.70 (m, 13H); 1.74 (d, J=7 Hz, 3H); 1.04 (t, l=7Hz, 3H).

IR(mull): $ñ_{max}$ 1603nd 1586 $cm^{-1}$.

MS: Calcd for $C_{17}H_{25}NO$: 259.1936. Found: 259.1934.

Analysis: Calcd for $C_{17}H_{25}NO.HCl$: C, 69.02; H, 8.86; N, 4.74 Found: C, 68.99, H, 8.84; N, 4.85.

2α,3,3a,β,4,5,9b ,β-hexahydro-9-methoxy-2-methyl-3-propyl-1H-benz[e]indole hydrochloride as a white solid top: 206°–207° C.

$^1$HNMR ($CDCl_3$, TMS): δ7.27–6.68 (m, 3H); 3.80 (s, 3H); 4.22–1.60 (m, 13 H); 1.70 (d, J=7 Hz, 3H); 1.03 (t, J=7Hz, 3H).

IR(mull): $ñ_{max}$ 1609 and 1578 $cm^{-1}$.

MS: Calcd for $C_{17}H_{25}NO$: 259.1936. Found: 259.1934.

Analysis: Calcd for $C_{17}H_{25}NO.HCl$: C, 69.02; H, 8.86; N, 4.47. Found: C, 68.14, H, 9.24; N, 4.87.

EXAMPLE 2

(+−)-2α,3,3a,α,4,5,9b,α-hexahydro-2-methyl-3-(2-propenyl)-1H-benz[ e]indol-9-ol hydrochloride (A-5, Chart A)

A solution of 1.0 mL (6.0 mmol) diphenylphosphine in 12 mL THF in a three-neck, round bottomed flask, equipped with a condenser and a septum, was treated with 4.4 mL (6.0 mmol) of n-butyllithium (1.6M in hexane) at 0° C. under a nitrogen atmosphere. The mixture was stirred at room temperature for 10 minutes and 0.77 g (3.0 mmol) cis-(+−)-1, 2,3,4-tetrahydro-8-methoxy-<N, 1-di-(2-propenyl)-2-naphthalenamine in 12 mL of THF was added. The red solution was refluxed (bath temperature 70° C.) for 48 hours. The reaction was quenched with water and extracted with ethyl acetate (2×500 mL). The organic layer was washed with brine, dried ($MgSO_4$), filtered and concentrated in vacuo to give a yellow oil. This oil was purified by liquid chromatography on 400 g silica gel 60 (230–400 m), eluting with 1 L 10% and 3 L 33% acetone/hexane, and collecting 40 mL fractions. Fractions 31–50 gave 0.32 g (44%) of free base as a light yellow oil. The oil was treated with excess anhydrous hydrochloric acid/methanol and concentrated in vacuo. Recrystallization from ethyl acetate-methanol afforded a white solid: mp.257°–258° C.

$^1$HNMR ($CDCl_3$, TMS): δ7.0–6.6 (m, 3H); 6.13–5.61 (m, 3H); 4.03–1.50 (m, 11H); 1.50, 1.48 (d, 3H).

IR (mull): $ñ_{max}$ 1606 and 1584 $cm^{-1}$.

MS: Calcd for $C_{16}H_{21}NO$: 243.1623. Found: 243.1621.

Analysis: Calcd for $C_{16}H_{21}NO.HCl$: C,68.68; H,7.93; N,5.01. Found: C,68.64; H,8.25; N,5.15.

EXAMPLE 3

Trans-(+−)-2α,3,3a,α,4,5,9b,α-hexahydro-2-methyl-3-propyl-1H-benz[e]indol- 9-ol hydrochloride (A-5, Chart A)

A solution of 1.3 g (5.0 mmol) of the free base of (+−)2α3,3aβ,4,5,9b,β-hexahydro- 9-methoxy-2-methyl-3-propyl-1H-benz[e]indole hydrochloride and 10 mL of 48% hydrobromic acid was refluxed (bath temperature 120° C.) for six hours. The mixture was cooled to room temperature and treated with 20% NaOH until pH>9. The mixture was extracted with ethyl acetate (2×1 L). The organic layer was washed with brine, dried ($MgSO_4$), filtered and concentrated in vacuo to give a tan colored solid. The solid was treated with excess HCl/MeOH and recrystallized from ethyl acetate/methanol to give 1.26 g (89%) as a white solid: top. 212°–213° C.

$^1$HNMR ($CDCl_3$, TMS): δ7.0–6.6 (m, 3H); 4.08–1.55 (m, 13H); 1.51 (d, J=7 Hz, 3H); 1.07 (t, J=7Hz, 3H).

IR (mull): $ñ_{max}$ 1610 and 1587 $cm^{-1}$.

MS: Calcd for $C_{16}H_{23}NO$: 245.1780. Found: 245.1799.

Analysis: Calcd for $C_{16}H_{23}NO.HCl$: C, 68.19; H, 8.58; N, 4.97. Found: C, 67.92, H, 8.69; N, 5.22.

Utilizing a procedure similar to that of Example 3 but using the appropriate starting material there is obtained:

cis-2,3,3a,4,5,9b-hexahydro-3-n-propyl-1H-benz[e]indol-9-ol hydrochloride as a white solid: mp. 223° C. (decomp)(B-5, Chart B)

$^1$HNMR ($CDCl_3$, TMS): δ7.95–6.61 (m, 3H); 3.50–1.50 (m, 14H); 0.97 (t, 3H).

IR(mull): $ñ_{max}$ 3172, 1609, and 1587 $cm^{-1}$.

MS: Calcd for $C_{15}H_{21}NO$: 231.1623. Found: 231.1625.

Analysis: Calcd for $C_{15}H_{21}NO.HCl$: C, 67.28; H, 8.28; N, 5.23. Found: C, 63.32; H, 8.01; N, 4.93.

Trans-(+−)-2.3,3a,4,9,9a-hexahydro-1-propyl-1H-benz[f]indol-5-ol hydrochloride as a white solid: mp. 180°–181° C. (B-5, Chart B)

$^1$HNMR ($CDCl_3$, TMS): δ8 7.04–6.58 (m, 3H); 3.38–1.45 (m, 15H); 0.94 (t, J=7Hz, 3H).

IR(mull): ñ$_{max}$ 1606 and 1580 cm$^{-1}$.

MS: Calcd for C$_{15}$H$_{21}$NO: 231.1623. Found: 231.1623.

Analysis: Calcd for C$_{16}$H$_{21}$NO.HCl: C, 77.88; H, 9.15; N, 6.05. Found: C, 77.76; H, 9.24; N, 6.06.

Cis-(+−)-2,3,3a,4,9,9a-hexahydro-1-propyl-1H-benz[f]indol-5-ol hydrochloride as a white solid: mp. 174°–175° C. (B-5, Chart B)

$^1$HNMR (CDCl$_3$, TMS): δ7.00–6.63 (m, 3H); 3.14–1.42 (m, 15H); 0.92 (t, J=7Hz, 3H).

IR(mull): ñ$_{max}$ 1611 and 1589 cm$^{-1}$.

MS: Calcd for C$_{15}$H$_{21}$NO: 231.1623. Found: 231.1625.

Analysis: Calcd for C$_{16}$H$_{21}$NO.HCl: C, 77.88; H, 9.15; N, 6.05. Found: C, 78.00; H, 9.03; N, 6.20.

EXAMPLE 4

Cis-(+−)-2,3,3a,4,5,9b-hexahydro-3-(2-propenyl)-1H-benz[e]indole hydrochloride (B-4, Chart B)

To a suspension of 3.15 g (83.2 mmol) of lithium aluminum hydride in 20 mL THF at 0° C. was added dropwise 4.74 g (20.8 mmol) of cis-(+−)-1,2,2a,4,5,9b-hexahydro-3-(2-propenyl)-2H-benz[e]-indol-2-one in 10 mL of THF. The solution was refluxed for 1.5 hours under a nitrogen atmosphere. TLC analysis showed no starting material remaining. The mixture was cooled to room temperature, transferred into an Erlenmeyer flask, and quenched at 0° C. by slow addition of saturated aqueous sodium sulfate. The mixture was diluted with 1 L ethyl acetate and dried over anhydrous sodium sulfate with vigorous stirring. The mixture was then filtered through a Celite pad, concentrated in vacuo. The resulting oil was purified by liquid chromatography on 400 g of silica gel 60 (230–400 m), eluting with hexane-ethyl acetate (1.5:1). Fractions homogeneous by TLC were combined and concentrated in vacuo to give 3 g (68%) of the desired product as a colorless oil. This oil was treated with excess HCl/MeOH and recrystallized from ethyl acetate/methanol as a white solid: mp. 170°–172° C.

$^1$HNMR (CDCl$_3$, TMS): δ7.18–7.12 (m, 4H); 6.36–5.51 (m, 3H); 4.10–3.90(m, 1H); 3.82–1.98 (m, 11H).

IR (mull): ñ$_{max}$ 1680 and 1598 cm$^{-1}$.

MS: Calcd for C$_{15}$H$_{19}$N: 213.1517. Found: 213.1515.

Analysis: Calcd for C$_{15}$H$_{19}$N.HCl: C, 72.13; H, 8.07; N, 5.60. Found: C, 71.82; H, 8.06; N, 5.55.

Utilizing a procedure similar to that of Example 4 but using the appropriate starting material there is obtained:

cis-(+−)-2,3,3a,4,5,9b-hexahydro-9-methoxy-3-(2-propenyl)-1H-benz[e]indole hydrochloride as a white solid: mp. 152°–154° C. (B-4, Chart B)

$^1$HNMR (CDCl$_3$, TMS): δ7.26–6.70 (m, 3H); 6.40–5.05 (m, 3H); 3.83 (s, 3H); 3.90–1.90 (m, 12H).

IR (mull): ñ$_{max}$ 1639, 1603 and 1585 cm$^{-1}$.

MS: Calcd for C$_{16}$H$_{21}$NO: 243.1623, Found: 243.1618.

Analysis: Calcd for C$_{16}$H$_{21}$NO.HCl: C, 68.68; H, 7.92; N, 5.01. Found: C, 68.74; H, 8.17; N, 4.97.

Cis-(+−)-2,3,3a,4,5,9b-hexahydro-6-methoxy-3-(2-propenyl)-1H-benz[e]indole hydrochloride as a white solid: mp. 173°–174° C. (B-4, Chart B).

$^1$HNMR (CDCl$_3$, TMS): δ7.16–6.70 (m, 3H); 6.73–5.45 (m, 3H); 3.82 (s, 3H); 4.80–1.36 (m, 12H).

IR (mull): ñ$_{max}$ 1647 and 1591 cm$^{-1}$.

MS: Calcd for C$_{16}$H$_{21}$NO: 243.1623. Found: 243.1630.

Analysis: Calcd for C$_{16}$H$_{21}$NO.HCl: C, 68.68; H, 7.92; N, 5.01. Found: C, 68.47; H, 8.26; N, 5.10.

Trans(+−)-2,3,3a,4,5,9b-hexahydro-6-methoxy-3-(2-propenyl)-1H-benz[e]indole hydrochloride as a white solid: top. 234°–235° C. (B-4, Chart B).

$^1$HNMR (CDCl$_3$, TMS): δ7.18–6.66 (m, 3H); 6.26–5.45 (m, 3H); 3.82 (s, 3H); 4.12–1.85 (m, 12H).

IR (mull): ñ$_{max}$ 1646 and 1583 cm$^{-1}$.

MS: Calcd for C$_{16}$H$_2$1NO: 243.1623, Found: 243.1635.

Analysis: Calcd for C$_{16}$H$_2$1NO.HCl: C, 68.68; H, 7.92; N, 5.01. Found: C, 68.55; H, 7.53; N, 5.31.

Trans-(+−)-2,3,3a,4,9,9a-hexahydro-8-methoxy-1-(2-propenyl)-1H-benz[f]indole hydrochloride as a white solid: top. 237°–239° C. (E-4, Chart E).

$^1$HNMR (CDCl$_3$, TMS): δ7.17–6.68 (m, 3H); 6.30–5.51 (m, 3H); 3.80 (s, 3H); 4.08–1.58 (m, 13H).

IR (mull): ñ$_{max}$ 1602 and 1583 cm$^{-1}$.

MS: Calcd for C$_{16}$H$_2$1NO: 243.1623. Found: 243.1615.

Analysis: Calcd for C$_{16}$H$_2$1NO.HCl: C, 68.68; H, 7.93; N, 5.01. Found: C, 68.38: H, 8.00; N, 5.01.

Cis-(+−)-2,3,3a,4,9,9a-hexahydro-8-methoxy-1-(2-propenyl)-1H-benz[f]indole hydrochloride as a white solid: top. 173°–174° C. (E-4, Chart E).

$^1$HNMR (CDCl$_3$, TMS): δδ 7.14–6.75 (m, 3H); 6.38–5.40 (m, 3H); 3.81 (s, 3H); 4.08–1.60 (m, 13H).

IR (mull): ñ$_{max}$ 1603 and 1587 cm$^{-1}$.

MS: Calcd for C$_{16}$H$_2$1NO: 243.1623. Found: 243.1617.

Analysis: Calcd for C$_{16}$H$_2$1NO.HCl: C, 68.68; H, 7.93; N, 5.01. Found: C, 68.80: H, 8.23; N, 5.08.

Trans-(+−)-2,3,3a,4,9,9a-hexahydro-5-methoxy-1-propyl-1H-benz[f]indole hydrochloride as a white solid: mp. 264°–265° C. (E-4, Chart E).

$^1$HNMR (CDCl$_3$, TMS): δδ 7.22–6.76 (m, 3H); 3.82 (s, 3H); 3.82–1.62 (m, 15H); 1.07 (t, 3H).

IR (mull): ñ$_{max}$ 1638 and 1582 cm$^{-1}$.

MS: Calcd for C$_{16}$H$_2$3NO: 245.1780. Found: 245.1781.

Analysis: Calcd for C$_{16}$H$_2$3NO.HCl: C, 68.19; H, 8.58; N, 4.98. Found: C, 68.09: H, 8.80; N, 5.05.

Cis-(+−)-2,3,3a,4,9,9a-hexahydro-5-methoxy-1-propyl-1H-benz[f]indole hydrochloride as a white solid: top. 250°–25 1° C. (E-4, Chart E).

$^1$HNMR (CDCl$_3$, TMS): δ7.22–6.86 (m, 3H); 3.81 (s, 3H); 3.81–1.58 (m, 15H); 1.05 (t, 3H).

IR (mull): ñ$_{max}$ 1605 and 1587 cm$^{-1}$.

MS: Calcd for C$_{16}$H$_2$3NO: 245.1780. Found: 245.1778.

Analysis: Calcd for C$_{16}$H$_2$3NO.HCl: C, 68.19; H, 8.58; N, 4.98. Found: C, 68.30: H, 8.72; N, 5.10.

Cis-(+−)-1,2,3,4,4a,5,6,10b-octahydro-10-methoxy-4-(2-propenyl-1H-benzo[ f]quinoline hydrochloride as a white solid: top. 231°–235° C. (B-4, Chart B).

$^1$HNMR (CDCl$_3$, TMS): δ7.12–6.68 (m, 3H); 6.50–5.51 (m, 3H); 3.79 (s, 3H); 3.90–1.90 (m, 15H).

IR (mull): ñ$_{max}$ 1601 and 1582 cm$^{-1}$.

MS: Calcd for C$_{17}$H$_2$3NO: 257.1780. Found: 257.1774.

Analysis: Calcd for C$_{17}$H$_2$3NO.HCl: C, 69.49; H, 8.23; N, 4.77. Found: C, 69.16; H, 8.30; N, 4.84.

Trans-(+−)-3,4,4a,5,10,10a-hexahydro-9-methoxy-1-(2-propenyl)-1H-benzo[g] quinoline hydrochloride as a white solid: mp. 236°–238° C. (F-4, Chart F).

$^1$HNMR (CDCl$_3$, TMS): δ7.14–6.65 (m, 3H); 6.13–5.52 (m, 3H); 3.80 (s, 3H); 3.92–1.18 (m, 15H).

IR (mull): $\tilde{n}_{max}$ 1590 cm$^{-1}$.

MS: Calcd for $C_{17}H_{23}NO$: 257.1780. Found: 257.1782.

Analysis: Calcd for $C_{17}H_{23}NO.HCl$: C, 69.49; H, 8.23; N, 4.77. Found: C, 69.48; H, 8.24; N, 4.84.

Cis-(+−)-3,4,4a,5,10,10a-hexahydro-9-methoxy-1-(2-propenyl)-1H-benzo[g]quinoline hydrochloride as a white solid: mp. 195°–197° C. (F-4, Chart F).

$^1$HNMR (CDCl$_3$, TMS: δ7.19–6.69 (m, 3H); 6.74–5.49 (m, 3H); 3.85 (s, 3H); 3.95–1.28 (m, 15H).

IR (mull): $\tilde{n}_{max}$ 1587 cm$^{-1}$.

MS: Calcd for $C_{17}H_{23}NO$: 257.1780. Found: 257.1777.

Analysis: Calcd for $C_{17}H_{23}NO.HCl$: C, 69.49; H, 8.23; N, 4.77. Found: C, 69.67; H, 8.45; N, 4.81.

Trans-2,3,3a,4,9,9a-hexahydro-5-methoxy-1-(2-propenyl-1H-benz[f]indole, hydrochloride as a white solid: m.p. 213°–215° C. (E-4, Chart E).

$^1$HNMR (CDCl$_3$, TMS: δ7.20–6.70 (m, 3H); 6.28–5.49 (m, 3H); 3.82 (s, 3H); 4.08–1.54 (m, 13H).

IR (mull): $\tilde{n}_{max}$ 1600 and 1583 cm$^{-1}$.

MS: Calcd for $C_{16}H_{21}NO$: 243.1623. Found: 243.1620.
Analysis: Calcd for $C_{16}H_{21}NO.HCl$: C, 68.68; H, 7.93; N, 5.01. Found: C, 68.44; H, 8.06; N, 5.20.

Cis-2,3,3a,4,9,9a-hexahydro-5-methoxy-1-(2-propenyl)-1H-benz[f]indole, hydrochloride as a white solid: m.p. 189°–191° C. (E-4, Chart E).

$^1$HNMR (CDCl$_3$, TMS: δ7.18–6.77 (m, ell); 6.38–5.42 (m, 3H); 3.82 (s, 3H); 3.98–1.60 M, 13H).

IR (mull): $\tilde{n}_{max}$ 1603 and 1588 cm$^{-1}$.

MS: Calcd for $C_{16}H_{21}NO$: 243.1623. Found: 243.1626.

Analysis: Calcd for $C_{16}H_{21}NO.HCl$: C, 68.68; H, 7.93; N, 5.01. Found: C, 68.32; H, 8.05; N, 5.10.

EXAMPLE 5

(Cis)-(+−)-1,2,3,4-tetrahydro-8-methoxy-2-(2-propenyl)-amino)-1-naphthalenemethanol hydrochloride as A (C-4, Chart 4) and (+−)-1,2,2a,-3,4,8b-hexahydro-8-methoxy-2-(prop-2-en-1-yl)-naphtho[2,1-B]azetidine hydrochloride as B (C- 5, Chart C)

A solution of 2.75 g (10 mmol) cis-(+−)-1,2,3,4-tetrahydro-8-methoxy-2-(2-propenylamino)- 1-naphthalenecarboxylic acid methyl ester in 110 mL of THF was added slowly 1.5 g (40 mmol) of lithium aluminum hydride at room temperature under a nitrogen atmosphere. The mixture was refluxed for two hours. The mixture was transferred into a 2-L Erlenmeyer flask equipped with a magnetic stirring bar and diluted with 1 L THF. The mixture was treated slowly with saturated aqueous sodium sulfate until the grey suspension became white. The mixture was stirred vigorously and dried (MgSO$_4$), filtered through a Celite pad, and concentrated in vacuo. The resulting yellow oil was purified by LC on 400 g silica gel 60 (230–400 m), eluting with hexane/acetone (9:1), and collecting 40 mL fractions. Fractions 36–62 afforded 2.37 g (96%) of an oil which later solidified. The solid was treated with HCl-methanol and recrystallized from ethyl acetate/methanol to give white solid A. (C-4, chart C): m.;. 203°–204° C. A solution of the free base of A (C-4,chart C) (1.24g, 5.0 mmol) and 1.14 g (60 mmol) of p-toluenesulfonyl chloride in 5 ml of pyridine was stirred at room temperature for 24 h. Additional 1.14 g (6.0 mmol) of p-toluenesulfonyl chloride was added and the mixture was heated for 3 h. the reaction was quenched with saturated sodium bicarbonate, extracted with ethyl acetate, washed with brine, dried (MgSO$_4$), filtered and concentrated in vacuo. The crude product was purified by LC eluting with hexane/acelate to give 0.32 g (26%) of the free base of B (C-5, chart C) This oil was treated with HCl-methanol and recrystallized from hexane-ethyl acetate-methanol to give pure B (C-5, Chart C) as a white solid: mp. 161°–162° C.

Physical data for A:

$^1$H NMR (CDCl$_3$, TMS): 7.20–6.65 (m,3H); 6.30–5.38 (m, 3H); 3.84 (s, 3H); 4.12–2.10 (m, 12H).

IR (mull): $v_{max}$ 3320, 1645, and 1585 cm$^{-1}$.

MS: Calcd for $C_{15}H_{21}NO_2$: 247.1572. Found: 247.1574.

Analysis: Calcd for $C_{15}H_{21}NO_2.HCl$: C, 63.48; H, 7.81; N, 4.94. Found: C, 63.14; H, 7.52; N, 4.95.

Physical data for B:

$^1$HNMR (CDCl$_3$, TMS): δ7.22–6.71 (m, 3H); 6.88–5.53 (m, 3H); 3.78 (s, 3H); 4.54–1.82 (m, 10H).

IR(mull): $\tilde{n}_{max}$ 1603 and 1587 cm$^{-1}$.

MS: Calcd for $C_{15}H_{29}NO$ (M$^+$+H): 230.1545. Found: 230.1545.

Analysis: Calcd for $C_{15}H_{19}NO.HCl$: C, 67.79; H, 7.59; N, 5.27. Found: C, 69.63; H, 7.84; N, 5.39.

EXAMPLE 6

Cis-(+−)-2,3,3a,4,5,9b-hexahydro-9-methoxy-3-n-propyl-1H-benz[e]indole hydrochloride (B-4, Chart B)

To a suspension of 3.63 g (95.7 mmol) of lithium aluminum hydride in 140 mL THF at 0° C. was added dropwise 5.9 g (23.7 mmol) of cis-(+−)-1,3,3a,4,5,9b-hexahydro-9-methoxy-3-(2-propyl)-2H-benz[e]-indol-2-one in 10 mL of THF. The solution was refluxed for two hours under a nitrogen atmosphere. TLC analysis showed no starting material remaining. The mixture was cooled to room temperature, transferred into an Erlenmeyer flask and quenched at 0° C. by slow addition of saturated aqueous sodium sulfate. The mixture was diluted with 1 L ethyl acetate and dried over anhydrous sodium sulfate with vigorous stirring. The mixture was then filtered through a Celite pad and concentrated in vacuo. The resulting oil was purified by liquid chromatography on 400 g of silica gel 60 (230–400 m), eluting with hexane-acetone (4:1). Fractions homogeneous by TLC were combined and concentrated in vacuo to give 4.64 g (83%) of the desired product as an oil. This oil was treated with excess HCl/MeOH and recrystallized from ethyl acetate/methanol as a white solid: mp. 153°– 156° C.

$^1$HNMR (CDCl$_3$, TMS): δ7.15–6.71 (m, 3H); 4.0 (t, 1H); 3.83 (s, 3H); 3.65– 1.75 (m, 13H); 1.03 (t, 3H).

IR (mull): $\tilde{n}_{max}$ 1601 and 1585 cm$^{-1}$.

MS: Calcd for $C_{16}H_{23}NO$: 245.1780. Found: 243.1788.

Analysis: Calcd for $C_{16}H_{23}NO.HCl$: C, 68.19; H, 8.58; N, 4.97. Found: C, 68.00; H, 8.56; N, 5.02.

Utilizing a procedure similar to that of Example 6 but using the appropriate starting material there is obtained:

Cis-(+−)-2,3,3a,4,5,9b-hexahydro-6-methoxy-3-n-propyl-1H-benz[e]indole hydrochloride as a white solid: mp. 197°–198° C.

$^1$HNMR (CDCl$_3$, TMS): δ7.16–6.70 (m, 3H); 3.82 (s, 3H); 4.12–1.92 (m, 14H); 1.03 (t, 3H).

IR (mull): $\tilde{n}_{max}$ 1660 and 1590 cm$^{-1}$.

MS: Calcd for $C_{16}H_{23}NO$: 245.1780. Found: 243.1799.

Analysis: Calcd for $C_{16}H_{23}NO \cdot HCl$: C, 68.19; H, 8.58; N, 4.97. Found: C, 67.91; H, 8.79; N, 5.09.

EXAMPLE 7

Cis(+—)-2α,3,3aα,4,9,9aα-hexahydro-8-methoxy-2-methyl-1-propyl-1H-benz[f]indole hydrochloride as A and
trans(+—)-2α,3,-3aβ,4,9,9aβ-hexahydro-8-methoxy-2-methyl-1-propyl-1H-benz[e]-indole hydrochloride as B (D-6, Chart D)

A solution of 3.89 g (15 mmol)cis-1,2,3,4-tetrahydro-8-methoxy-3-2-propenyl-2-naphthalenamine and 14.3 g (45 mmol) of mercuric acetate in 450 mL of methanol was stirred at room temperature under a nitrogen atmosphere for three days. TLC analysis appeared to show no starting material remaining (the aliquot was quenched with small amount of sodium hydroxide/sodium borohydride). The greenish-gray mixture was the treated with a solution containing 2.27 g (60 mmol) sodium borohydride in 60 mL 20% sodium hydroxide and the resulting mixture was stirred vigorously for three hours. Methanol was removed under reduced pressure and the concentrate was extracted with methylene chloride (2×1 L). The combined organic layers were washed with brine, dried ($MgSO_4$), filtered and concentrated in vacuo. The resulting oil was purified by liquid chromatography on 800 g of silica gel 60 (230–400 m), eluting with hexaneacetone( 4:1) and collecting 40 mL fractions. Fractions 26–34 afforded 2.2 g which was repurified again to give 2.05 (53%) of the cyclized product as a light yellow oil (free base of A) and fractions 35–48 gave 0.72 g (18%) of a brown oil, identified by $^1HNMR$ as the recovered starting material. Fractions 49–80 gave a brown oil which was repurified again to give 0.33 g (8.5%) of the other cyclized product as a yellow oil (free base of the trans isomer B). Both of the cyclized products were converted into HCl-salt by treating with excess HCl/methanol (prepared by adding acetyl chloride to methanol at 0° C. and recrystallized from ethyl acetate/hexane. From the less polar product (the major product), pure cis isomer of the title compound A was obtained as a white solid: mp. 240°–242° C. From the more polar product (the minor product), pure trans isomer of the title compound was obtained as a white solid: top. 180°–182° C.

Physical data for A:

$^1HNMR$ (CDCl$_3$, TMS): δ7.13–6.74 (m, 3H); 3.81 (s, 3H); 3.71–1.72 (m, 13H); 1.69 (d, J=7 Hz, 3H); 1.08 (t, J=7Hz, 3H). H); IR(mull): ñ$_{max}$ 1605nd 1587 cm$^{-1}$. H); MS: Calcd for $C_{17}H_{25}NO$: 259.1936. Found: 259.1939.

Analysis: Calcd for $C_{17}H_{25}NO \cdot HCl$: C, 69.02; H, 8.86; N, 4.74. Found: C, 68.38, H, 8.69; N, 4.98.

Physical data for B:

$^1HNMR$ (CDCl$_3$, TMS): δ7.16–6.74 (m, 3H); 3.81 (s, 3H); 4.15–1.60 (m, 13H); 1.23 (d, J=7 Hz, 3H); 1.04 (t, J=7Hz, 3H).

IR(mull): ñ$_{max}$ 1603 and 1586 cm$^{-1}$.

MS: Calcd for $C_{17}H_{25}NO$: 259.1936. Found: 259.1931.

Analysis: Calcd for $C_{17}H_{25}NO \cdot HCl$: C, 69.02; H, 8.86; N, 4.47. Found: C, 68.30, H, 9.09; N, 4.75.

FORMULA

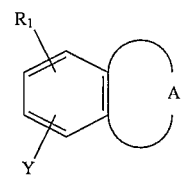

I

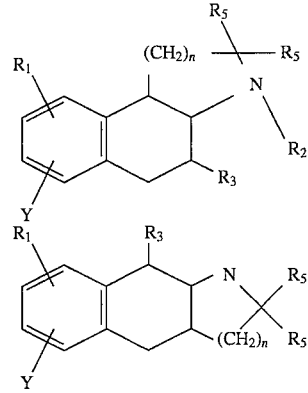

Ia

Ib

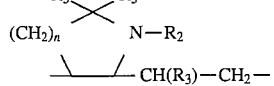

a

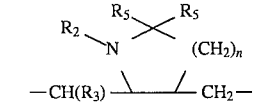

b

CHART A

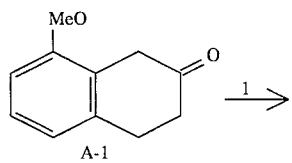

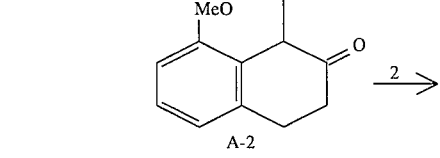

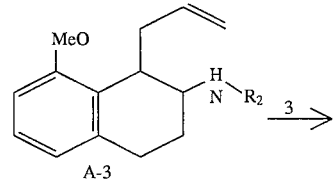

-continued
CHART A
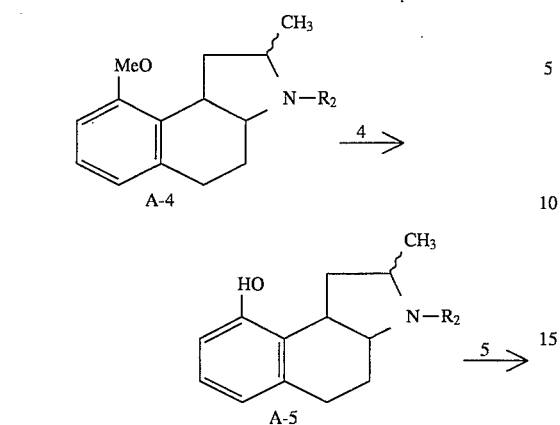
CHART B
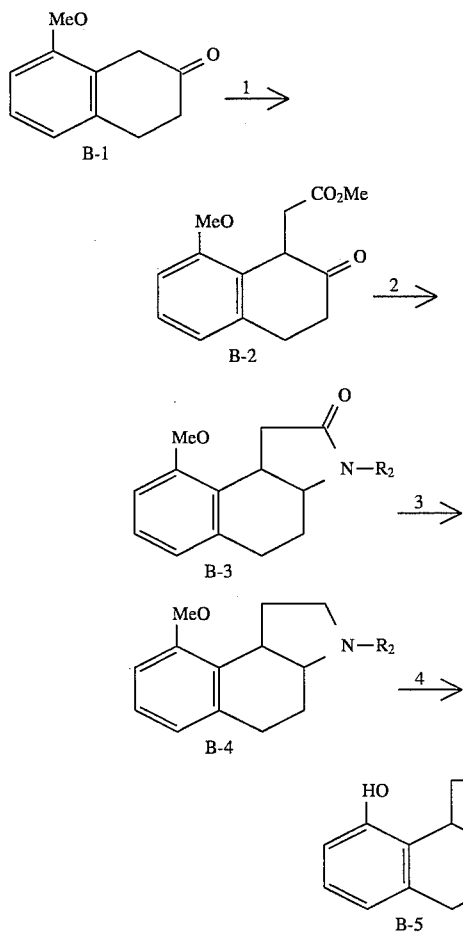
CHART C
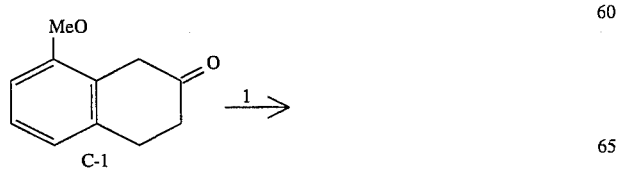
-continued
CHART C
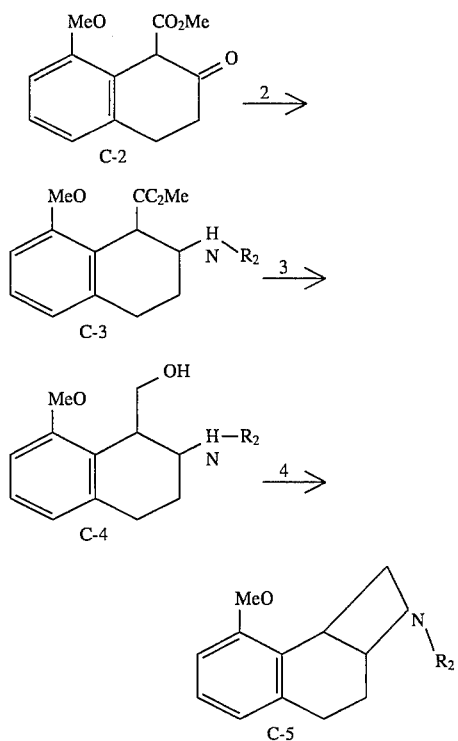
CHART D
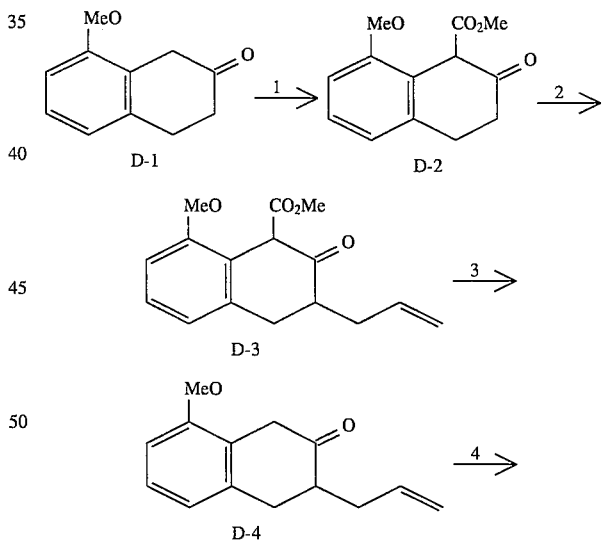

-continued
CHART D

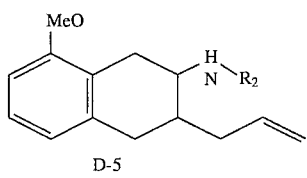

D-5

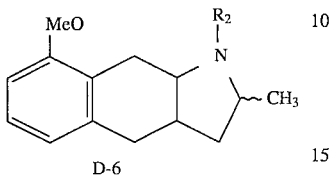

D-6

CHART E

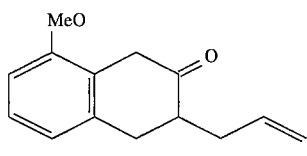

E-1

↓ 1

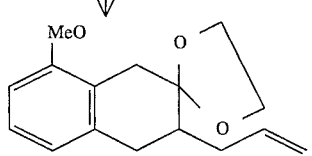

E-2

↓ 2

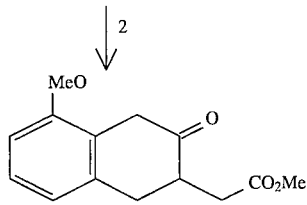

E-3

↓ 3

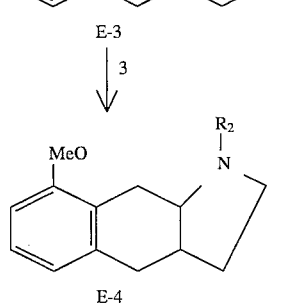

E-4

CHART F

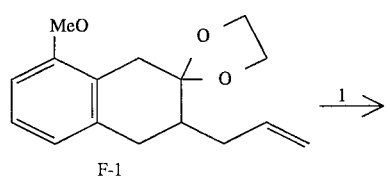

F-1

-continued
CHART F

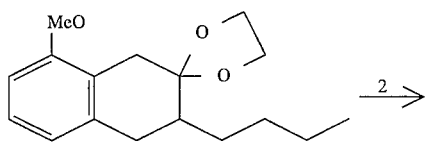

F-2

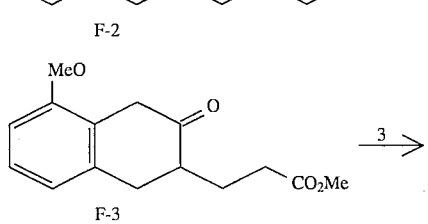

F-3

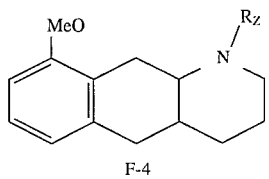

F-4

I claim:
1. A compound having the formula

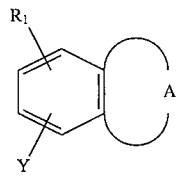   I where Y is hydrogen or halogen
wherein $R_1$ is
  (a) hydrogen
  (b) —$OR_4$
  (c) —$SR_4$
  (d) —$OSO_2CF_3$
  (e) —$CONR_6R_6$ (except that when A is (a) only one $R_6$ can be hydrogen)
  (f) —CO—(2-pyrrolyl)
wherein A is

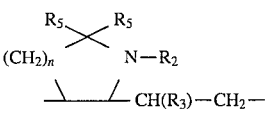   a a or

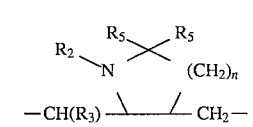   b wherein $R_2$ is
  (a) -hydrogen
  (b) —($C_1$–$C_8$) alkyl
  (c) —($C_3$–$C_8$) alkenyl
  (d) —($C_3$–$C_8$) alkynyl
  (e) —$(CH_2)_m$—($C_3$–$C_8$)cycloalkyl
  (f) —$(CH_2)_m$—($C_3$–$C_8$)cycloalkenyl
  (j) —$(CH_2)_m$-aryl (h) —$(CH_2)_m$—$CO_2R_6$ wherein $R_3$ is
(a) -hydrogen
(b) —$(C_1-C_4)$alkyl
(c) -aryl
(d) —$(CH_2)_n$—CO—$(C_1-C_4)$alkyl
(e) —CO-aryl wherein $R_4$ and $R_5$ are
(a) -hydrogen
(b) —$(C_1-C_4)$-alkyl
(c) —$(C_2-C_4)$alkenyl
(d) -aryl wherein $R_6$ is
(a) -hydrogen
(b) —$(C_1-C_4)$alkyl
(c) -aryl wherein m is 1 to 4 and n is 0 or 1 with the provisos that when A is formula a and Y is hydrogen, $R_2$ is hydrogen or methyl and n is 1, then $R_1$ cannot be hydrogen, hydroxy or alkoxy.

2. A compound of claim 1 having the formula

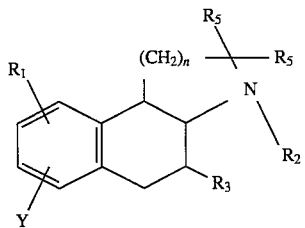

Ia wherein $R_1$, $R_2$, $R_3$ and $R_5$, Y and n are the same as in claim 1.

3. A compound according to claim 2 wherein n is 1.

4. A compound according to claim 3 selected from the group of
(2α,3αα,9bα)-2,3,3a,4,5,9b-hexahydro-9-methoxy-2-methyl-3-propyl-1H-benz[e] indole hydrochloride;
(2α,3αβ,9bβ)-2,3,3a,4,5,9b-hexahydro-9-methoxy-2-methyl-3-propyl- 1H-benz[e]indole hydrochloride;
(2α,3aα,9bα)-2,3,3α,4,5,9b,hexahydro-2-methyl-3-propyl-1H-benz[e] indol-9-ol hydrochloride;
(2α,3aα,9bα)-2,3,3α,4,5,9b-hexahydro-2-methyl-3-(2-propenyl)- 1H-(benz[e]indol-9-ol, hydrochloride;
cis-2,3,3a,4,5,9b-hexahydro-9-methoxy-3-(2-propenyl)-1H-benz[e]indole hydrochloride;
(2α,3aα,9bα)-2,3,3a,4,5,9b-hexahydro-2-methyl-3-propyl)-1H-benz[e] indol hydrochloride;
cis-2,3,3a,4,5,9b-hexahydro-6-methoxy-3-(2-propenyl)-1H-benz[e]indole hydrochloride;
trans-2,3,3a,4,5,9b-hexahydro-6-methoxy-3-(2-propenyl)-1H-benz[e]indole hydrochloride;
cis-2,3,3a,4,5,9b-hexahydro-6-methoxy-3-propyl-1H-benz[e]indole hydrochloride;
cis-2,3,3a,4,5,9b-hexahydro-3-(2-propenyl)-1H-benz[e]indole hydrochloride;
cis-2,3,3a,4,5,9b-hexahydro-9-methoxy-1(H)-benz[e]indole hydrochloride;
cis-(1S,2R)-2,3,3a,4,5,9b-hexahydro-6-methoxy-3-(2-propenyl)-1(H)-benz[e] indole hydrochloride;
cis-(1R,2S)-2,3,3a,4,5,9b-hexahydro-6-methoxy-3-(2-propenyl)-1(H)-benz[e] indole hydrochloride.

5. A claim according to claim 4, selected from the group consisting of cis-2,3,3a,4,5,9b-hexahydro-6-methoxy-3-(2-propenyl)-1H-benz[e]indole hydrochloride;
trans-2,3,3a,4,5,9b-hexahydro-6-methoxy-3-(2-propenyl)-1H-benz[e]indole hydrochloride;
cis-2,3,3a,4,5,9b-hexahydro-6-methoxy-3-n-propyl-1H-benz[e]-indole hydrochloride;
cis-2,3,3a,4,5,9b-hexahydro-3-(2-propenyl)-1H-benz[e]-indole hydrochloride;
cis-2,3,3a,4,5,9b-hexahydro-9-methoxy-3-(2-propenyl)-1H-benz[e]indole hydrochloride;
cis-2,3,3a,4,5,9b-hexahydro-9-methoxy-1(H)-benz[e]indole hydrochloride;
cis-(1S,2R)-2,3,3a,4,5,9b-hexahydro-6-methoxy-3-(2-propenyl)-1(H)-benz[e] indole hydrochloride;
cis-(1R,2S)-2,3,3a,4,5,9b-hexahydro-6-methoxy-3-(2-propenyl)-1(H)-benz[e] indole hydrochloride.

6. A compound according to claim 4 wherein n is 1.

7. A compound according to claim 1 having the formula

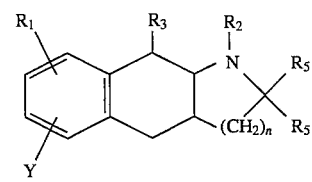

Ib wherein $R_1$, $R_2$, $R_3$ $R_5$, Y and n are the same as in claim 1.

8. A compound according to claim 6,
trans-2,3,3a,4,9,9a-hexahydro-5-methoxy-1-propyl-2H-benz[f]indole hydrochloride;
cis-2,3,3a,4,9,9a-hexahydro-5-methoxy-1-propyl-1H-benz [f]-indole hydrochloride;
trans-2,3,3a,4,9,9a-hexahydro-propyl-1H-benz[f]indol-5-ol;
cis-2,3,3a,4,9,9a-hexahydro-1-propyl-1H-benz[f]indol-5-ol;
(2α,3aβ,9aβ)-2,3,3a,4,9,9a-hexahydro-8-methoxy-2-methyl-1-propyl- 1H-benz[f]indole hydrochloride;
(2α,3aα,9aα)-2,3,3a,4,9,9a-hexahydro-8-methoxy-2-methyl-1-propyl- 1H-benz[f]indole hydrochloride;
trans-2,3,3a,4,9,9a-hexahydro-8-methoxy-1-(2-propenyl)-1H-benz[f]indole hydrochloride;
cis-2,3,3a,4,9,9a-hexahydro-8-methoxy-1-(2-propenyl)-1H-benz [f]indole hydrochloride;
trans-2,3,3a,4,9,9a-hexahydro-5-methoxy-1-(2-propenyl)-1H-benz[f]indole hydrochloride;
cis-2,3,3a,4,9,9a-hexahydro-5-methoxy-1-(2-propenyl)-1H-benz[f]indole hydrochloride;
trans-(2R,3R)-2,3,3a,4,9,9a-hexahydro-5-methoxy-1-(2-propenyl)-1(H)-ben[f]indole hydrochloride;
trans-(2S,3S)-2,3,3a,4,9,9a-hexahydro-5-methoxy-1-(2-propenyl)-1(H)-ben[f]indole hydrochloride.

9. A compound according to claim 2, wherein n is 0.

10. A compound according to claim 9, selected from the group consisting of
cis-1,2,2a,3,4,8b-hexahydro-8-methoxy-2-(prop-2-en-1-yl)-naphtho[2.1. B]-azetidinehydrochloride,
cis-1,2,2a,3,4, 8b-hexahydro-2-n-propylnaphtho[2.1.B]-azetidine hydrochloride,
cis-1,2,2a,3,4, 8b-hexahydro-2-n-[propylnaphtho[2.1.B]-azetidine hydrochloride.

* * * * *